(12) United States Patent
Tiwari et al.

(10) Patent No.: US 9,255,285 B2
(45) Date of Patent: Feb. 9, 2016

(54) FERMENTATION MEDIAS AND PROCESSES THEREOF

(71) Applicant: BIOCON LIMITED, Bangalore, Karnataka (IN)

(72) Inventors: Sanjay Tiwari, Karnataka (IN); Mukesh Babuappa Patale, Maharashtra (IN); Saurabh Garg, Uttaranchal (IN); Mayank Kumar Garg, Uttar Pradesh (IN); Sulekha Joshi, Karnataka (IN); Chittnalli Ramegowda Naveen Kumar, Bangalore (IN); Bimal Kumar, Patna (IN); Anuj Goel, Karnataka (IN); Harish Iyer, Karnataka (IN)

(73) Assignee: Biocon Limited (IN)

( * ) Notice: Subject to any disclaimer, the term of this patent is extended or adjusted under 35 U.S.C. 154(b) by 0 days.

(21) Appl. No.: 14/162,382

(22) Filed: Jan. 23, 2014

(65) Prior Publication Data

US 2014/0141467 A1 May 22, 2014

Related U.S. Application Data

(62) Division of application No. 12/866,453, filed as application No. PCT/IN2009/000078 on Feb. 5, 2009, now Pat. No. 8,927,256.

(30) Foreign Application Priority Data

Feb. 6, 2008 (IN) .......................... 00310/CHE/2008
Jan. 12, 2009 (IN) .......................... 00086/CHE/2009

(51) Int. Cl.
| | | |
|---|---|---|
| *C12N 1/00* | (2006.01) | |
| *C12P 21/04* | (2006.01) | |
| *C12N 9/00* | (2006.01) | |
| *C12P 21/00* | (2006.01) | |
| *C07K 14/535* | (2006.01) | |
| *C12N 9/20* | (2006.01) | |
| *C12N 9/52* | (2006.01) | |
| *C12P 21/02* | (2006.01) | |

(52) U.S. Cl.
CPC .............. *C12P 21/00* (2013.01); *C07K 14/535* (2013.01); *C12N 9/20* (2013.01); *C12N 9/52* (2013.01); *C12P 21/02* (2013.01)

(58) Field of Classification Search
None
See application file for complete search history.

(56) References Cited

U.S. PATENT DOCUMENTS 4,288,554 A 9/1981 Zotti et al.
8,927,256 B2 1/2015 Tiwari et al.

2004/0253692 A1 12/2004 Lee et al.
2010/0317056 A1 12/2010 Tiwari et al.
2014/0141467 A1* 5/2014 Tiwari .................... C12P 21/02
435/69.1

FOREIGN PATENT DOCUMENTS

| WO | WO-0056903 A2 | 9/2000 |
| WO | WO-2004039996 A1 | 5/2004 |
| WO | WO-2005052174 A2 | 6/2005 |
| WO | WO-2007005646 A2 | 1/2007 |

OTHER PUBLICATIONS

"U.S. Appl. No. 12/866,453, Final Office Action mailed Jun. 6, 2014", 5 pgs.
"U.S. Appl. No. 12/866,453, Final Office Action mailed Jul. 8, 2013", 5 pgs.
"U.S. Appl. No. 12/866,453, Non Final Office Action mailed Dec. 20, 2013", 9 pgs.
"U.S. Appl. No. 12/866,453, Non Final Office Action mailed Dec. 21, 2012", 5 pgs.
"U.S. Appl. No. 12/866,453, Notice of Allowance mailed Aug. 25, 2014", 6 pgs.
"U.S. Appl. No. 12/866,453, Preliminary Amendment filed Aug. 5, 2010", 6 pgs.
"U.S. Appl. No. 12/866,453, Response filed Mar. 20, 2013 to Non Final Office Action mailed Dec. 21, 2012", 7 pgs.
"U.S. Appl. No. 12/866,453, Response filed Mar. 20, 2014 to Non Final Office Action mailed Dec. 20, 2013", 9 pgs.
"U.S. Appl. No. 12/866,453, Response filed Aug. 6, 2014 to Final Office Action mailed Jun. 6, 2014", 7 pgs.
"U.S. Appl. No. 12/866,453, Response filed Oct. 8, 2013 to Final Office Action mailed Jul. 8, 2013", 12 pgs.
"U.S. Appl. No. 12/866,453, Response filed Nov. 9, 2012 to Restriction Requirement mailed Oct. 9, 2012", 8 pgs.
"U.S. Appl. No. 12/866,453, Restriction Requirement mailed Oct. 9, 2012", 7 pgs.
"International Application Serial No. PCT/IN2009/000078, International Search Report mailed Sep. 7, 2009", 7 pgs.
"International Application Serial No. PCT/IN2009/000078, Written Opinion mailed Sep. 7, 2009", 9 pgs.
Bensinger, et al., "Autologous Transplantation with Peripheral Blood Mononuclear Cells Collected After Administration of Recombinant Granulocyte Stimulating Factor", Blood, vol. 81, No. 11, (1993), 3158-3163.
Cregg, J M, "Development of the Methylotrophic Yeast, *Pichia pastoris*, as a Host System for the Production of Foreign Proteins", Developments in Industrial Microbiology, vol. 29., (1988), 33-41.
Cregg, J M, "Recent Advances in the Expression of Foreign Genes in Pichia pastoris", Nature Biotechnology, vol. 11, No. 8., (1993), 905-910.

(Continued)

*Primary Examiner* — Michael Burkhart
(74) *Attorney, Agent, or Firm* — Schwegman Lundberg & Woessner, P.A.

(57) ABSTRACT

The present invention demonstrates the utility of carbonic acid amides such as urea or its derivatives, carbamates, carbodiimides & thiocarbamides as nitrogenous supplements in fermentation media for production of recombinant proteins to achieve enhanced bioconversion rates and peptides like insulin and insulin analogs, exendin and enzymes such as lipase using methanol inducible fungal expression systems such as *Pichia*.

10 Claims, 27 Drawing Sheets

(56) References Cited

OTHER PUBLICATIONS

Metcalf, D., "The molecular biology and functions of the granulocyte-macrophage colony-stimulating factors", Blood, 67(2), (Feb. 1986), 257-267.

Narasaki, T, et al., "Studies on the Lipoprotein Lipases of Microorganisms. Part II. Effects of Culture Conditions on the Production of Lipoprotein Lipases by *Pseudomonas* sp. M-12-33", Agricultural and Biological Chemistry, vol. 32, No. 12,, (1968), 1453-1457.

Neben, S, et al., "Mobilization of Hematopoietic Stem and Progenitor Cell Subpopulations from the Marrow to the Blood of Mice Following Cyclophosphamide and/or Granulocyte Colony-Stimulating Factor", Blood, vol. 81, No. 7., (1993), 1960-1967.

Roberts, A W, et al., "Granulocyte Colony-Stimulating Factor Induces Selective Elevations of Progenitor Cells in the Peripheral Blood of Mice", Experimental Hematology, vol. 22., (1994), 1156-1163.

Yan, et al., "Mobilization of Long-Term Hematopoietic Reconstituting Cells in Mice by the Combination of Stem Cell Factor Plus Granulocyte Colony-Stimulating Factor", Blood, vol. 84, No. 3., (1994), 795-799.

\* cited by examiner

FERMENTATION MEDIAS AND PROCESSES THEREOF

CROSS-REFERENCE TO RELATED APPLICATION

This application is a divisional of U.S. patent application Ser. No. 12/866,453, filed on Aug. 5, 2010, which is the National Stage of International Application No. PCT/IN2009/00078, filed on Feb. 5, 2009, which claims the benefit of India Pat. App. No 00310/CHE/2008, filed on Feb. 6, 2008, and India Pat. App. No. 00086/CHE/2009, filed on Jan. 12, 2009, all of which are herein incorporated by reference in their entirety.

FIELD OF THE INVENTION

The present invention demonstrates the utility of carbonic acid amides such as urea or its derivatives, carbamates, carbodiimides & thiocarbamides as nitrogenous supplements in fermentation media for production of recombinant proteins to achieve enhanced bioconversion rates and peptides like insulin and insulin analogues, exendin and enzymes such as lipase using methanol inducible fungal expression systems such as Pichia. The significant aspects of the invention specifically relate to an improvised fermentation process with optimized nutritional media parameters responsible for higher product yield in shorter production periods. The principle of the present invention can also be applied for production of a wide range of proteins and secondary metabolites through fermentation of a suitable expression organism.

BACKGROUND AND PRIOR ART OF THE INVENTION

Yeast based expression systems such as Pichia pastoris are commonly used to express recombinant proteins Cregg, J. M. et al., in Dev. Ind. Microbiol. 29:33-41; 1988. The P. pastoris expression system uses the methanol-induced alcohol oxidase (AOX1) promoter, which controls the gene that codes for the expression of alcohol oxidase, the enzyme which catalyzes the first step in the metabolism of methanol Cregg J M. et al. in Bio/Technology 11: 905-910; 1993. P. pastoris has potential for high expression levels, efficient secretion of extracellular protein, post-translational modifications such as glycosylation, and growth to high cell densities on minimal medium in bioreactor cultures.

Fed batch fermentation process using Pichia pastoris is described in "Pichia fermentation Process Guidelines" of Invitrogen Co. (San Diego, Calif.), hereafter referred to as control. For production of recombinant proteins transformed Pichia pastoris is grown to a desired high cell density biomass on glycerol as carbon source. Production phase is initiated by feeding of methanol which serves as inducer and sole carbon source to the culture. During biomass generation and production phase ammonia is used to control pH which serves as nitrogen source.

Albeit the various advantages conferred by Yeast Expression Systems, there still exists need for optimizing the nutritionally influenced physico-chemical environment for efficient and maximal recombinant protein production in bioreactors. Achieving high specific productivity is highly desirable. It can be obtained by optimization of initial media composition, methanol feeding strategy and process physico-chemical parameters. There are reports wherein ammonium sulfate, ammonium phosphate, di ammonium phosphate, potassium nitrate, urea, corn steep liquor, soya bean meal, cotton seed meal, cane and beet molasses, peptones, meal hydrolysates etc have been used as nitrogen source for bacterial, yeast and fungal growth. Use of different carbon and nitrogen sources for 'growth' of a microbe is a prior art.

However, the optimum combination of specifically defined carbon and nitrogen sources for efficient production of recombinant proteins, peptides and enzymes has not been disclosed in prior art literature. For example, WO/2007/005646 discloses ethanol production per se, by cultivating recombinant yeasts on complex growth medium containing complex carbohydrates as well as a variety of cheaper nitrogen sources like corn steep liquor, corn extract, yeast autolysate and urea. Further, this process does not utilize the methanol inducible machinery for growth or production unlike the process developed in the present invention for production of recombinant proteins. Similarly, a U.S. Pat. No. 4,288,554 describes a continuous fermentation process for merely growth of a non GMO Candida species using urea in combination with other sources of nitrogen and basal salt medium. There is no suggestion or teaching whatsoever where urea can be used during fermentation process (batch, fed batch, continuous) using methanol inducible GMO Pichia pastoris for efficient production of recombinant proteins and peptides like human insulin and its analogues or enzymes like lipase.

It has been surprisingly found that the use of defined fermentation medium characterized by controlled addition of certain rich and readily soluble nitrogenous sources such as urea further in optimized concentrations with respect to the residual concentrations of urea as well as residual concentrations of ammonia generated from urea hydrolysis enables higher product, productivity and thus lesser production time. Production of recombinant proteins using E coli has been known for years and the expression system is clearly studied and understood. E coli based expression system has been widely used for the production of molecules like GCSF, HGH, Streptokinase and many other similar biological products. For production of recombinant proteins transformed E. coli is grown to a desired high cell density biomass on dextrose as carbon source. Production phase is initiated by induction using a required inducer and then the culture is just maintained with minimal feeding of nutrients till the end of fermentation.

Fungal cultures had been used since ages for the production of valuable bio-entities like enzymes and other commodity molecules. Fungal cultures like Rhizopus, Aspergillus, Penicillium, etc have been used in classical fermentation for the production of wide variety of enzymes like lipases, amylases, dextranases, etc which are used in food, textile, leather and other such industries. Actinomycetes, known as workhorses for antibiotics production, have being used extensively for the production of several secondary metabolites beneficial for human kind. One of the key properties of fungi and actinomycetes is their property for "bioconversion", like hydroxylation, esterification etc. The major advantage is that the bioconversions are target specific and products with relatively high purity can be obtained. A classical example is the conversion of compactin to pravastatin.

Methodological improvements known in art include measures relating to fermentation technology, such as stirring or supplying with oxygen, or modification relating to composition of the nutrient media such as the modifying sugar concentrations during the fermentation, down-stream processing changes, or changes related to the intrinsic properties of the microorganism itself etc It has been surprisingly found that the use of fermentation medium characterized by controlled addition of certain rich and readily soluble nitrogenous sources such as urea enables higher productivity and/or higher rate of bioconversion and thus lesser production time.

OBJECTIVES OF THE INVENTION

The main objective of the present invention is to obtain a fermentation medium for production of recombinant proteins its derivatives or analogs thereof by fermentation using methanol inducible fungal species.

Another main objective of the present invention is to obtain a fermentation medium for production of recombinant proteins, their derivatives or analogs thereof by fermentation using microorganisms.

Yet another main objective of the present invention is to obtain a fermentation medium for the production of secondary metabolites by fermentation using microorganisms. Still another main objective of the present invention is to obtain a process for production of recombinant or non recombinant protein products their derivatives or analogs thereof.

Still another main objective of the present invention is to obtain a process for production of secondary metabolites.

Still another main objective of the present invention is to obtain a process of bioconversion of compactin to pravastatin Still another main objective of the present invention is to obtain a recombinant protein product.

STATEMENT OF THE INVENTION

Accordingly, the present invention relates to a fermentation medium for production of recombinant proteins, its derivatives or analogs thereof by fermentation using methanol inducible fungal species, said medium characterized in that it consists an effective concentration of a carbonic acid amide; a fermentation medium for production of recombinant proteins, their derivatives or analogs thereof by fermentation using microorganisms, said medium characterized in that it consists an effective concentration of a carbonic acid amide; a fermentation medium for the production of secondary metabolites by fermentation using microorganisms, said medium characterized in that it consists an effective concentration of a carbonic acid amide; a process for production of recombinant proteins, its derivatives or analogs thereof which comprises propagating a methanol inducible insulin expressing fungal species in a fermentation medium, said medium characterized in that it consists an effective concentration of a carbonic acid amide; a process for production of recombinant or non-recombinant protein products, their derivatives or analogs thereof which comprises propagating an inducible or non-inducible protein expressing microorganism in a fermentation medium, said medium characterized in that it consists an effective concentration of a carbonic acid amide; a process for production of secondary metabolites which comprises propagating a microorganism in a fermentation medium said medium characterized in that it consists an effective concentration of a carbonic acid amide; a process of bioconversion of compactin to pravastatin, said conversion is effectuated in a medium, characterized in that said medium contains an effective concentration of a carbonic acid amide; and a recombinant protein product obtained as claimed in any of the preceding claims.

DETAILED DESCRIPTION OF THE INVENTION

Figure 1:
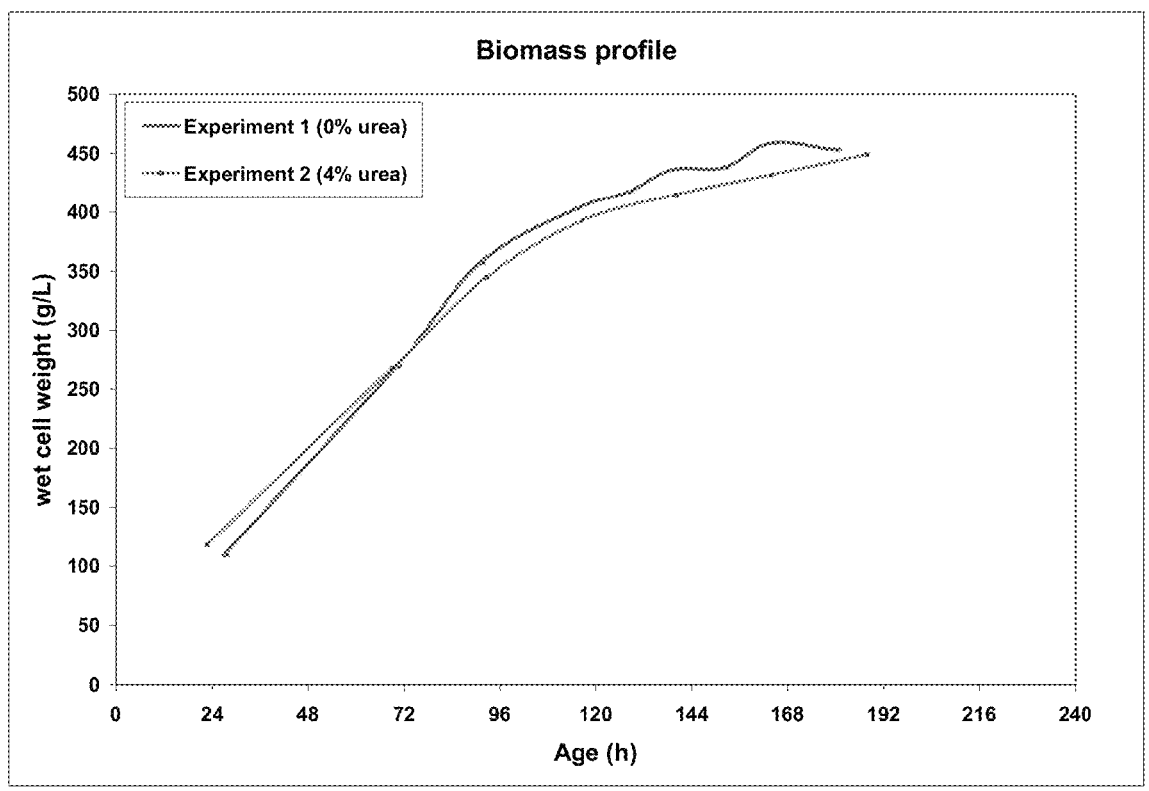
FIG. 1: Comparison of biomass profile of IN-105 precursor with/without urea addition.

The present invention relates to a fermentation medium for production of recombinant proteins, its derivatives or analogs thereof by fermentation using methanol inducible fungal species, said medium characterized in that it consists an effective concentration of a carbonic acid amide.

In another embodiment of the present invention, the carbonic acid amide is selected from the group comprising urea or its derivatives such as dimethylurea, diethylurea, N-acetylphenyl urea, isopropylpylideneurea, phenylurea or combination thereof.

In yet another embodiment of the present invention, the carbonic acid amide is urea.

In still another embodiment of the present invention, the carbonic acid amide is added in liquid, spray, powder or pellet form.

In still another embodiment of the present invention, residual concentration of carbonic acid amide is up to 1 M.

In still another embodiment of the present invention, concentrations of basal salts and trace elements is varied from 0.1× to 5× of the control medium, keeping residual concentration of carbonic acid amide upto 1 M.

In still another embodiment of the present invention, uptake of phosphate is improved. In still another embodiment of the present invention, the methanol inducible fungal species expressing the recombinant insulin product are selected from the group comprising *Pichia pastoris, Pichia* sp., *Saccharomyces* sp., *Saccharomyces cerevisiae, Kluyveromyces* sp., or *Hansenula polymorpha*.

The present invention relates to a fermentation medium for production of recombinant proteins, their derivatives or analogs thereof by fermentation using microorganisms, said medium characterized in that it consists an effective concentration of a carbonic acid amide.

The present invention relates to a fermentation medium for the production of secondary metabolites by fermentation using microorganisms, said medium characterized in that it consists an effective concentration of a carbonic acid amide.

In another embodiment of the present invention, the carbonic acid amide is selected from the group comprising urea or its derivatives such as dimethylurea, diethylurea, N-acetylphenyl urea, isopropylpylideneurea, phenylurea or combination thereof.

In yet another embodiment of the present invention, the carbonic acid amide is urea.

In still another embodiment of the present invention, the carbonic acid amide is added in liquid, spray, powder or pellet form.

In still another embodiment of the present invention, the residual concentration of carbonic acid amide is upto 10 g/L.

In still another embodiment of the present invention, the micro-organism are selected from the group comprising *E. coli, Streptomyces* sp, *Aspergillus* sp, *Rhizopus* sp, *Penillium* sp and *Rhizomucor* sp.

The present invention relates to a process for production of recombinant proteins, its derivatives or analogs thereof which comprises propagating a methanol inducible insulin expressing fungal species in a fermentation medium, said medium characterized in that it consists an effective concentration of a carbonic acid amide.

In another embodiment of the present invention, the carbonic acid amide is selected from the group comprising urea or its derivatives such as dimethylurea, diethylurea, N-acetylphenyl urea, isopropylpylideneurea, phenylurea or combination thereof.

In yet another embodiment of the present invention, the carbonic acid amide is urea.

In still another embodiment of the instant invention, the recombinant insulin product produced is IN-105.

In still another embodiment of the present invention, the recombinant insulin product produced is an insulin precursor, insulin or their analogues or derivatives thereof.

In still another embodiment of the present invention, the recombinant insulin product is insulin glargine.

In still another embodiment of the present invention, the recombinant protein produced is a cyclic or non-cyclic peptide.

In still another embodiment of the present invention, the recombinant peptide is exendin.

In still another embodiment of the present invention, the recombinant protein produced is a enzyme.

In still another embodiment of the present invention, the recombinant enzyme product produced is lipase.

In still another embodiment of the present invention, the recombinant protein produced is selected from a group comprising an insulin precursor, insulin or their analogues or derivatives thereof, glargine, exendin, carboxypeptidase and lipase.

In still another embodiment of the present invention, the methanol inducible fungal species expressing the recombinant insulin product are selected from the group comprising *Pichia pastoris, Pichia* sp., *Saccharomyces* sp., *Saccharomyces cerevisiae, Kluyveromyces* sp., or *Hansenula polymorpha*.

In still another embodiment of the present invention, the methanol inducible fungal species is *Pichia pastoris*.

In still another embodiment of the present invention, the methanol feeding rate is up to 20 g/L of broth per h.

In still another embodiment of the present invention, the maximum product titre obtained is above 0.1 g/L.

The present invention relates to a process for production of recombinant or non-recombinant protein products, their derivatives or analogs thereof which comprises propagating an inducible or non-inducible protein expressing microorganism in a fermentation medium, said medium characterized in that it consists an effective concentration of a carbonic acid amide.

In another embodiment of the present invention, the carbonic acid amide is selected from the group comprising urea or its derivatives such as dimethylurea, diethylurea, N-acetylphenyl urea, isopropylpylideneurea, phenylurea or combination thereof.

In yet another embodiment of the present invention, the carbonic acid amide is urea.

In still another embodiment of the present invention, the recombinant protein product produced is G-CSF.

In still another embodiment of the present invention, the recombinant product produced is streptokinase.

In still another embodiment of the present invention, the protein product is lipase.

The present invention relates to a process for production of secondary metabolites which comprises propagating a microorganism in a fermentation medium said medium characterized in that it consists an effective concentration of a carbonic acid amide.

In another embodiment of the present invention, the secondary metabolite produced is pravastatin.

The present invention relates to a process of bioconversion of compactin to pravastatin, said conversion is effectuated in a medium, characterized in that said medium contains an effective concentration of a carbonic acid amide.

In another embodiment of the present invention, the carbonic acid amide is selected from the group comprising urea or its derivatives such as dimethylurea, diethylurea, N-acetylphenyl urea, isopropylpylideneurea, phenylurea or combination thereof.

In yet another embodiment of the present invention, the bioconversion of compactin to pravastatin is at least 35%.

The present invention relates to a recombinant protein product obtained as above.

In another embodiment of the present invention, the recombinant protein product obtained is selected from a group comprising insulin precursor, insulin or their analogues or derivatives thereof, glargine, exendin, carboxypeptidase and lipase.

The invention provides a nutrient composition for use in formulating a fermentation medium, which composition comprises nitrogenous components such as carbonic acid amides like urea and related forms or derivatives mentioned earlier, together with one or more other fermentation media components that have been specifically optimized to obtain higher insulin or related analogues of derivative product yields in shorter production time periods.

It has been surprisingly found that the use of a particular fermentation medium supplemented with certain nitrogenated sources such as carbonic acid amides like urea and related forms or derivatives in specific concentrations do not affect the growth of yeast cells, rather help in improving productivity.

The additional nitrogenous component like urea may be added in liquid, spray, powder or pellet form.

The crux of the invention resides in the fact that the productivity of the insulin or insulin analogue fermentation process by *Pichia* sp. is influenced greatly by the urea content of the culture medium. Therefore the yield of product is considerably increased especially in reduced fermentation time periods by addition of a nitrogenous component such as urea in the culture medium According to the most preferred embodiment of the invention, urea addition to the fermention medium improves the consumption rate of a key ingredient 'phosphate' which intern improves the productivity. It has been found that the faster the consumption of phosphate, the lesser is the fermentation cycle time and hence higher is the productivity. Thus, it is the newly observed metabolism of urea along with phosphate that increases the rate of protein or peptide expression without affecting the growth profile and reduces the time of fermentation.

According to another aspect of the invention, addition of urea permits increased product recovery at the end of fermentation at any pH.

The present invention thereby enables greater yields of protein product, lesser production cycle times, better utilization of the nutrients fed into a process, and in general reduces capital and production costs.

A suitable microbial strain for an industrial fermentation process using a chemically defined medium may be any wild type strain producing a valuable compound of interest, provided that said wild type strain has a good growth performance Preferred yeasts for use as production organism include e.g. *Pichia pastoris, Pichia* sp., *Saccharomyces* sp., *Saccharomyces cerevisiae, Kluyveromyces* sp., or *Hansenula polymorpha*.

In addition, a suitable microbial strain for an industrial fermentation process using a chemically defined medium may be a strain which is obtained and/or improved by subjecting a parent strain of interest to a classical mutagenic treatment or to recombinant DNA transformation, also with the provision that the resulting mutant or transformed microbial strain has a good growth performance on a chemically defined medium. It will thereby depend on the growth performance of the parent strain on a chemically defined medium whether the resulting mutant or transformed strains should have an improved or a similar growth performance on a chemically defined medium as compared to that of the parent strain.

As a person skilled in art would cognize, the optimal concentration of the carbonic acid amide supplements would vary from clone to clone, though the end result is obtaining higher titer in lesser time in all cases.

"Fermentation media" or "fermentation medium" refers to the environment in which the fermentation is carried out which includes the fermentation substrates and other raw materials utilized by the fermenting microorganisms to produce the specific therapeutic product.

"Nitrogenous components" are substrates, raw materials or components which are a source of assimilable nitrogen in the fermentation medium.

According to a significant aspect of the invention, the preferred nitrogenous component in the fermentation media is carbonic acid amides such as urea. This would include compounds containing N—CO—N or related groups. Use of derivatives of urea such as dimethylurea, diethylurea, N-acetyl-N-phenylurea, Isopropyllideneurea, N-phenyl urea and the like or combinations thereof are contemplated by the present invention.

The "effective amount" employed is that quantity of urea or its derivatives which according to the invention when introduced into the fermentation medium an appreciable quantity/yield of the protein is produced, further in lesser time periods without affecting the growth of yeast cells.

"Fermenting Organism" refers to any microorganism suitable for use in a desired fermentation process. Examples of fermentating organisms include fungal organisms such as yeasts. Examples of fermenting organisms in context of the present invention are *Pichia pastoris, Pichia* sp., *Saccharomyces* sp., *Saccharomyces cerevisiae, Kluyveromyces* sp., or *Hansenula polymorpha*.

The invention may be suitable for any recombinant peptide expression using methanol inducible fungal species, but are not limited recombinantly expressed peptides, proteins, insulin, insulin precursors, insulin derivatives or insulin analogues.

The term "recombinant", as used herein to describe a protein or polypeptide means a polypeptide produced by expression of a recombinant polynucleotide. The term "recombinant", as used herein in reference to cells, means cells that can be or have been used as recipients for recombinant vectors or other transfer DNA, and include progeny of the original cell which has been transfected. It shall be understood that progeny of a single parental cell may not be completely identical in morphology or in genomic or total DNA complement to the original parent, due to accidental or deliberate mutation. The term 'polypeptide', 'protein', 'peptide' refers to a polymer of amino acids and does not refer to a specific length of the product; thus, peptides, oligopeptides, and proteins are included within the definition of polypeptide. This term also does not refer to or exclude post-expression modifications of the polypeptide although chemical or post-expression modifications of these polypeptides may be included or excluded as specific embodiments. In one embodiment, the molecule is a polypeptide or their related analogs or derivatives thereof. Preferably, the polypeptide is a cyclic peptide. According to another preferred embodiment, the polypeptide is a non-cyclic peptide. In still another preferred embodiment, the polypeptide is selected from the group comprising exendin, eptifibatide, atosiban, enzymes such as lipase, carboxypeptidase and the like.

Insulin is a polypeptide of 51 amino acids which are distributed between two amino acid chains: the A chain with 21 amino acids and the B chain with 30 amino acids. The chains are connected to one another by 2 disulfide bridges. This includes the use not only of naturally occurring insulins but also of insulin derivatives and analogs. The insulin compound may, for example, be a mammalian insulin compound, such as human insulin, or an insulin compound derivatives or analogs.

Insulin derivatives are derivatives of naturally occurring insulins, namely human insulin or animal insulins, which differ from the corresponding, otherwise identical naturally occurring insulin by substitution of at least one naturally occurring amino acid residue and/or addition of at least one amino acid residue and/or organic residue. It is understood that the term insulin defines a polypeptide composed out of a B- and A-chain. The insulin derivative may be at least 60% homologous to a naturally occurring insulin. The insulin derivative may be even more homologous, such as at least about 75%, or at least about 90%, homologous to a naturally occurring insulin. In general, insulin derivatives have a slightly modified action compared with human insulin.

When producing insulin and insulin derivatives by genetic engineering, an insulin precursor, "proinsulin", comprising B, C and A chains is frequently expressed. Said proinsulin can be converted into insulin or an insulin derivative by enzymatic or chemical removal of the C chain after appropriate and correct folding and formation of the disulfides bridges. Proinsulin derivative may be at least 60% homologous in B- and A-chain of a naturally occurring proinsulin. The connecting C-peptide, however, may be chosen as being totally different from any known natural occurring C-peptide. The proinsulin derivative may be even more homologous, such as at least about 75%, or at least about 90%, homologous to a naturally occurring proinsulin.

According certain embodiments of the invention the recombinant insulin product is IN-105. The resultant therapeutic product specifically relates to the molecule IN-105. IN-105 is an insulin molecule conjugated at the epsilon amino acid Lysine at position B29 of the insulin B-chain with an ampiphilic oligomer of structural formula $CH_3O—(C_4H_2O)_3—CH_2—CH_2—COOH$. The molecule may be monoconjugated at A1, B1 and B29, di-conjugated at various combinations of A1, B1 and B29, or triconjugated at various combinations of A1, B1 and B29.

According to another aspect of the invention, the recombinant protein produced via fermentation utilizing the fermentation medium of the present invention is a cyclic or non-cyclic peptide.

According to another aspect of the invention, the recombinant protein produced via fermentation utilizing the fermentation medium of the present invention is an enzyme. In one aspect of the invention, the fermentation protocol may comprise of three phases: Batch, fed-batch (optional) and methanol induction phase.

According to the most significant aspect of the invention, the fermentation medium used in context of the subject invention comprises the following components. Also embodied is the process of preparing the medium.

Medium Composition:

| Components | Quantity (g/L) |
|---|---|
| $CaSO_4•2H_2O$ | 0.93 |
| $MgSO_4•7H_2O$ | 29.8 |
| $K_2SO_4$ | 36.4 |
| KOH | 4.13 |
| Glycerol | 40 |
| $H_3PO_4$ (Density-1.7) | 22.95 |
| Urea | 6.0 |

The individual components were dissolved in minimal volume of water in the above-mentioned sequence and sterilized at 121° C. for 1 hour. The trace salt solution and D-biotin (pre-sterilised by filtration) was added aseptically to the medium, each at the rate of 4.35 ml/L of medium (density of trace salts solution is 1.05 and that of D-biotin is 1.0.

Composition of Trace Salt Solution:

| Components (Salts) | Quantity (g/L) |
|---|---|
| Copper sulphate, $CuSO_4•5H_2O$ | 6.0 |
| Sodium iodide, NaI | 0.08 |
| Manganese sulphate, $MnSO_4•H_2O$ | 3.0 |
| Sodium molybdate, $Na_2MoO_4•2H_2O$ | 0.20 |
| Boric acid, $H_3BO_3$ | 0.02 |
| Cobalt chloride, $CoCl_2•6H_2O$ | 0.50 |
| Zinc chloride, $ZnCl_2$ | 20.0 |
| Ferrous sulphate, $FeSO_4•7H_2O$ | 65.0 |
| Sulphuric acid, $H_2SO_4$ | 5.0 mL |

All the salts were dissolved one by one in potable water and were sterilized by filtration through sterilizing grade filtration apparatus.

Biotin Solution Preparation:

| | |
|---|---|
| D-Biotin | 0.2 g/L |

Biotin was dissolved in potable water and sterilized by filtration through sterilizing grade filtration apparatus.

Yeast Extract and Soy Peptone Feed:

Additionally, Yeast Extract and Soy Peptone (YEP) feed was also added during fermentation. It is to be prepared as follows:

| Components | Conc. (g/L) |
|---|---|
| Soy Peptone | 100 |
| Yeast extract | 50 |

The components were dissolved and volume was made up with potable water as required. The solution was then sterilized at 121°-123° C. for 90 min. The density of YEP feed was around 1.05.

Methanol Feed:

12.0 ml of trace salt solution, 12 mL of D-biotin solutions and 40 g of Urea were added per liter of methanol before feeding.

Fermentation Process:

The fermentation process includes a batch cell growth phase, an optional glycerol fed batch phase and methanol induction phase.

Batch Cell Growth Phase

Batch Monitoring and Control

Production fermenter parameters are initially set and controlled as follows:

Temperature: 30°±2° C.
pH: 5±0.2
DO: >10%
Run Time: 22-24 hr

Methanol Induction Phase (MIP)

Methanol feeding was started immediately after the end of Batch phase. Methanol was sterilized (online) by filtration using a commercially available sterilizing grade filter.

At the beginning of MIP, the pH was adjusted to 4.0±0.1 or 6.0±0.1 or 6.3±0.1 depending upon expression of protein into the medium (Varies from product to product as well as clone to clone), and the temperature was adjusted to about 18-24 degree C. (varies from product to product and also clone to clone)

Simultaneously, another feed, yeast extract and Soy peptone feed (YEP) was also started in the fermenter at the rate of 0.4 g/L/h of starting volume.

MIP Monitoring and Control
Temperature: 18 to 30° C. (varies from product to product as well as clone to clone)
pH: 3.0 to 7.0
DO: >1% (used to control methanol concentration in broth)
Run Time:5-8 days (varies from clone to clone)
Assay pH:1-9.5 (depending upon protein type)

According to another aspect of the invention, the inoculum is prepared by cultivating lyophilized glycerol stock culture to minimal glycerol (MGY) medium. The basal fermentor media has been derived from "Control Pichia process guidelines" contains ortho-phosphoric acid, calcium sulfate dehydrated, potassium sulfate, magnesium sulfate hepta hydrated, potassium hydroxide, glycerol, trace salts and D-biotin. The nutrient culture medium must also contain known compounds in small or trace amounts which are usually incorporated in fermentation culture media such as water soluble compounds of Ca, Mg, Mn, Fe, K, Co, Cu, Zn, B, Mo, Br and I. Other trace salts may also be present. Trace salts solution of the present invention specifically include cupric sulfate penta hydrated, sodium iodide, manganese sulfate mono hydrated. Sodium molybdate di hydrated, boric acid, cobalt chloride hexa hydrated, zinc chloride, ferrous sulfate hepta hydrated. Though concentration of each medium ingredient has been optimized specifically for each product, given below is the control media:

Control Media
Fermentation Basal Salts Medium:
For a 1 liter, mix together the following ingredients:
Phosphoric acid:85% (26.7 ml)
Calcium sulfate:0.93 g
Potassium sulfate:18.2 g
Magnesium sulfate-7H2O:14.9 g
Potassium hydroxide:4.13 g
Glycerol:40.0 g
Water to 1 Liter Add to fermenter with water to the appropriate volume and sterilize.

PTM1 Trace Salts
Mix together the following ingredients:

| Cupric sulfate5H2O | 6.0 g |
| Sodium iodide | 0.08 g |
| Manganese sulfate-H2O | 3.0 g |
| Sodium molybdate-2H2O | 0.2 g |
| Boric Acid | 0.02 g |
| Cobalt chloride | 0.5 g |
| Zinc chloride | 20.0 g |
| Ferrous sulfate-7H2O | 65.0 g |
| Biotin | 0.2 g |
| Sulfuric Acid | 5.0 ml |

Water to a final volume of 1 liter
Filter, sterilize and store at room temperature.

There may be a cloudy precipitate upon mixing of these ingredients. The media may be filtered, sterilized and used.

In addition to above control medium, urea is included at different concentrations. According to yet another aspect of the invention, biomass generation during batch phase is until glycerol is present in initial medium. Further, biomass generation is not critical and is done in only few cases.

According to a further aspect of the invention, after desired biomass is achieved, culture is induced by continuous feeding of methanol and urea. During methanol feeding yeast extract and peptone solution is also fed.

According to yet another aspect, the methanol feeding rate is upto 20 g/L/h. As any skilled artisan would cognize, optimizations of feeding rate to further improve production levels are contemplated by the present invention.

While the invention will now be described in connection with certain preferred embodiments in the following examples so that aspects thereof may be more fully understood and appreciated. It is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of fermentation procedures as well as of the principles and conceptual aspects of the invention.

The invention provides a nutrient composition for use in formulating a fermentation medium, which composition comprises nitrogenous components such as carbamides like urea and related forms or derivatives like carbamates, carbodiimides, thiocarbamides together with one or more other fermentation media components that has been specifically optimized to obtain higher product yields in shorter production time periods.

The invention thus makes it possible to obtain better yields of recombinant protein products such as insulin, glargine IN105, exendin, lipase and carboxypeptidase during fermentation process (batch, fed batch, continuous) using methanol inducible GMO Pichia pastoris enabled through addition of urea without affecting growth of the yeast cells.

According to one aspect of the invention, the nitrogenous component that specifically impacts the production yields and time are carbonic acid amides such as urea or their derivatives and related compounds mentioned earlier.

According to another aspect of the invention, preferred yeasts for use as production organism include e.g. Pichia pastoris, Pichia sp., Saccharomyces sp., Saccharomyces cerevisiae, Kluyveromyces sp., or Hansenula polymorpha.

The present invention demonstrates the utility of carbonic acid amides such as urea or its derivatives, carbamates, carbodiimides & thiocarbamides as nitrogenous supplements in fermentation media for production of proteins to achieve enhanced bioconversion rates using E. coli, Actinomycetes and fungal cultures. The significant aspects of the invention specifically relate to an improvised fermentation process with optimized nutritional media parameters responsible for higher productivity. The principle of the present invention can be applied for production of a wide range of proteins and secondary metabolites through fermentation of a suitable expression organism.

The invention provides a nutrient composition for use in formulating a fermentation medium, in which composition comprises nitrogenous components such as carbamides like urea and related forms or derivatives like carbamates, carbodiimides, thiocarbamides together with one or more other fermentation media components that has been specifically optimized to obtain higher product yields in shorter production time periods.

The invention thus makes it possible to obtain better yields of protein products such as GCSF, Sterptokinase, HGH and others during fermentation process (batch, fed batch, continuous) using inducible E. coli enabled through addition of urea without affecting growth of the yeast cells.

The invention also makes it possible to improve the rate of bioconversion obtain better yields of products such as Pravastatinduring fermentation process (batch, fed batch, continuous) using actinomycetes and/or fungal cultures.

The instant invention also enhances the rate of production of enzymes like Lipase, amylases, cellulases in batch or fed batch processes using fungal cultures.

According to one aspect of the invention, the nitrogenous component that specifically impacts the production yields and time are carbonic acid amides such as urea or their derivatives and related compounds mentioned earlier.

According to another aspect of the invention, preferred microorganisms are strains of the Enterobacteriaceae family preferably for use as production organism include but not limiting to E. coli.

According to another aspect of the invention, preferred microorganisms are strains of actinomycetes and/or fungal family including but not limiting to *Streptomyces* sp, *actinoplanes* sp, *Aspergillus* sp, *Rhizopus* sp and *Penicillium* sp.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

The invention provides a nutrient composition for use in formulating a fermentation medium, in which composition comprises nitrogenous components such as carbonic acid amides like urea and related forms or derivatives mentioned earlier, together with one or more other fermentation media components that have been specifically optimized to obtain desired protein product or secondary metabolites.

It has been surprisingly found that the use of a particular fermentation medium supplemented with certain nitrogenated sources such as carbonic acid amides like urea and related forms or derivatives in specific concentrations do not affect the growth of fermenting organism, rather helps in improving productivity.

The additional nitrogenous component like urea may be added in liquid, spray, powder or pellet form.

A suitable microbial strain for an industrial fermentation process may be any wild type strain producing a valuable compound of interest, provided that said wild type strain has a good growth performance In addition, a suitable microbial strain for an industrial fermentation process may be a strain which is obtained and/or improved by subjecting a parent strain of interest to a classical mutagenic treatment or to recombinant DNA transformation, also with the provision that the resulting mutant or transformed microbial strain has a good growth performance. It will thereby depend on the growth performance of the parent strain whether the resulting mutant or transformed strains should have an improved or a similar growth performance as compared to that of the parent strain.

The fermentation process using the instant fermentation medium is improved, with regard to one or more of the parameters selected from the group consisting of the product concentration (product per volume), the product yield (product formed per carbon source consumed) and the product formation (product formed per volume and time), or else other process parameters and combinations thereof.

As a person skilled in art would recognize, the optimal concentration of the carbonic acid amide supplements would vary from clone to clone, though the end result is obtaining higher titer in lesser time in all cases.

"Fermentation media" or "fermentation medium" refers to the environment in which the fermentation is carried out which includes the fermentation substrates and other raw materials utilized by the fermenting microorganisms to produce the specific therapeutic product.

The Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and other ingredients cornsteep liquor, sugar beet molasses, glycerol and barley malt. Additionally the carbon substrate may also be one-carbon substrates such as carbon dioxide, or methanol for which metabolic conversion into key biochemical intermediates has been demonstrated. Hence it is contemplated that the source of carbon utilized in the present invention may encompass a wide variety of carbon containing substrates and will only be limited by the choice of organism. In addition to an appropriate carbon source, the fermentation media must contain suitable minerals, salts, buffers and other components, known to those skilled in the art, suitable for the growth of the cultures and promotion of the expression of the desired protein or end product.

"Nitrogenous components" are substrates, raw materials or components which are a source of assimilable nitrogen in the fermentation medium.

Suitable nitrogen sources may include but are not limted to soya flour, cotton seed flour, peptones, yeast extract, casein, casein hydrolysates, corn steep liquor and inorganic salts of ammonium ion, nitrates and nitrites.

According to a significant aspect of the invention, the preferred supplement in the fermentation media is carbonic acid amides such as urea. This would include compounds containing N—CO—N or related groups. Use of derivatives of urea such as dimethylurea, diethylurea, N-acetyl-N-phenylurea, Isopropyllideneurea, N-phenyl urea and the like or combinations thereof are contemplated by the present invention.

The "effective amount" employed is that quantity of urea or its derivatives which according to the invention when introduced into the fermentation medium, an appreciable quantity/yield of the product is produced, further in lesser time periods without affecting the growth of the fermenting organism.

"Fermenting Organism" refers to any microorganism suitable for use in a desired fermentation process. According to another aspect of the invention, preferred microorganisms are strains bacteria, actinomycetes and/or fungal species preferably for use as production organism include but not limiting to *E. coli, Streptomyces* sp, *actinoplanes* sp, *Aspergillus* sp, *Rhizopus* sp, *Penicillium* sp, etc The term "recombinant", as used herein to describe a protein or polypeptide means a polypeptide produced by expression of a recombinant polynucleotide. The term "recombinant", as used herein in reference to cells, means cells that can be or have been used as recipients for recombinant vectors or other transfer DNA, and include progeny of the original cell which has been transfected. It shall be understood that progeny of a single parental cell may not be completely identical in morphology or in genomic or total DNA complement to the original parent, due to accidental or deliberate mutation.

The term 'polypeptide', 'protein', 'peptide' refers to a polymer of amino acids and does not refer to a specific length of the product; thus, peptides, oligopeptides, and proteins are included within the definition of polypeptide. This term also does not refer to or exclude post-expression modifications of the polypeptide although chemical or post-expression modifications of these polypeptides may be included or excluded as specific embodiments. In one embodiment, the molecule is a polypeptide or their related analogs or derivatives thereof. Preferably, the polypeptide is a cyclic peptide. According to another preferred embodiment, the polypeptide is a non-cyclic peptide. According to another aspect of the invention, the recombinant protein is produced via fermentation utilizing the fermentation medium of the present invention.

One of the embodiments of the present invention relates to the production of GCSF (Granulocyte Colony stimulating factor). Granulocyte colony stimulating factor (GCSF), is a pharmaceutically active protein which regulates proliferation, differentiation, and functional activation of neutrophilic granulocytes (Metcalf, Blood 67:257 (1986); Yan, et al. Blood 84(3): 795-799 (1994); Bensinger, et al. Blood 81(11): 3158-3163 (1993); Roberts, et al., Expt'l Hematology 22: 1156-1163 (1994); Neben, et al. Blood 81(7): 1960-1967 (1993)). GCSF is meant the natural or recombinant protein, preferably human, as obtained from any conventional source such as tissues, protein synthesis, cell culture with natural or recombinant cells. Any protein having the activity of GCSF, such as muteins or otherwise modified proteins, is encompassed.

A "secondary metabolite" is a compound, derived from primary metabolites, that is produced by an organism, is not a primary metabolite and is not required for growth of the microorganism under standard conditions. Secondary metabolite compounds can be converted to useful compounds by subsequent chemical conversion or subsequent biotransformation. As such, providing improved availability of such intermediate compounds would still lead to improved production of the ultimate useful compound, which itself may be referred to herein as a secondary metabolite.

In one aspect of the invention, the fermentation protocol may comprise of two phases: Batch and fed-batch (optional)

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions. These examples should not be construed to limit the scope of the invention. The following Examples represent preferred embodiments of the present invention.

Example 1

Figure 2:
FIG. 2: Comparison of product concentration profile of IN-105 precursor with/without urea addition.

Two fermentor batches were run using *Pichia pastoris* for expression of IN105 precursor. In one batch (experiment #1) half of control media strength is taken as initial medium except glycerol. After batch run methanol is fed at about 8 g/L/h feed rate. Fermentation is continued for ~8 days. Maximum product concentration reached to 3.0 g/L within 7 days and stabilized. In another batch (experiment #2) same media composition is used and additionally 0.1 M urea is added to fermentor. After batch run methanol along with 4% w/v urea is fed. Fermentation was continued for 8 days. Maximum product concentration reached to 3.5 within 7 days. There was no significant difference observed on cell growth profile. Biomass and product concentration profiles resulting from the above experimentation are represented in FIGS. 1 & 2 respectively.

Example 2

Figure 3:
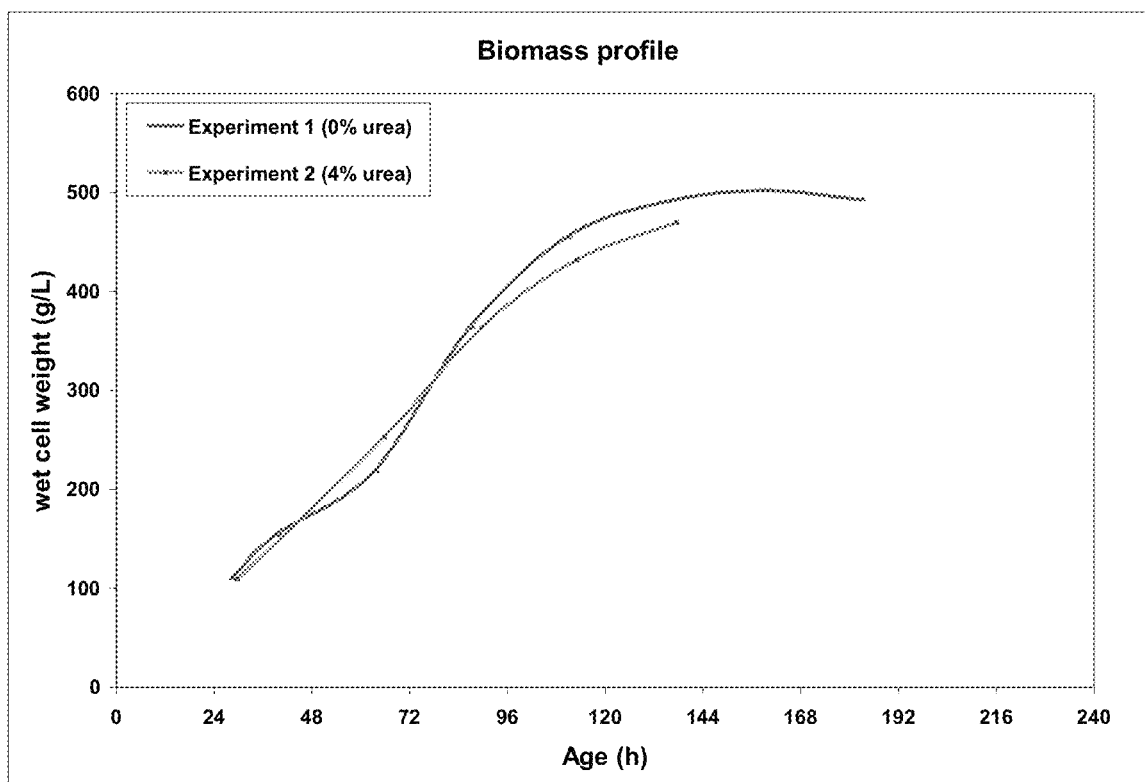
FIG. 3: Comparison of biomass profile of Insulin precursor with/without urea addition.
Figure 4:
FIG. 4: Comparison of product concentration profile of Insulin precursor with/without urea addition.

Expression of Insulin precursor with urea was studied using *Pichia pastoris* fermentation to ascertain the rate of product expression. In this trial control media composition was used and methanol with 4% urea was fed at higher rate of 20 g/L/h. In this trial maximum product concentration achieved 4.21 g/L in 137 as against 4.26 g/L in 182 hours when urea was not added to the fermentor. No difference in cell growth profile was observed indicating that urea addition to the fermentor increased the rate of product expression without affecting the growth profile and reduced the time of fermentation. Biomass and product concentration profiles resulting from the above experimentation are represented in FIGS. 3 & 4 respectively.

Example 3

Figure 5:
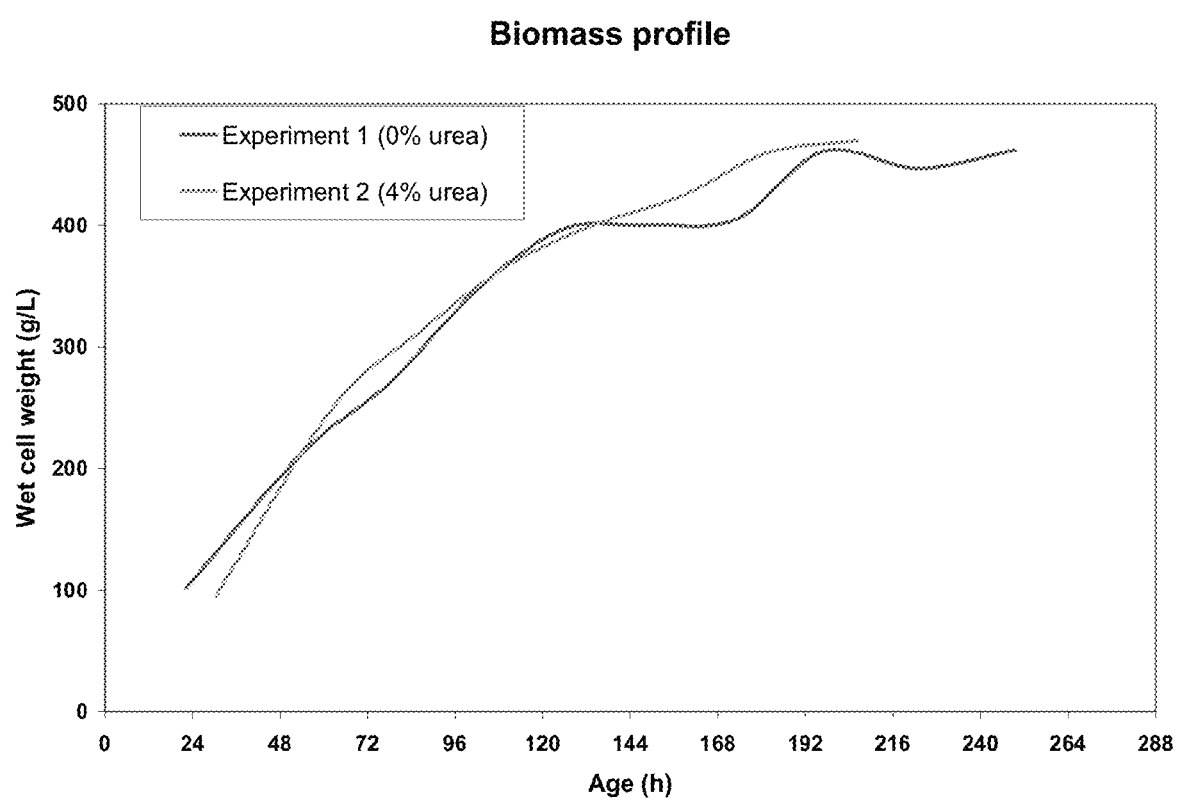
FIG. 5: Comparison of biomass profile of Glargine precursor with/without urea addition.
Figure 6:
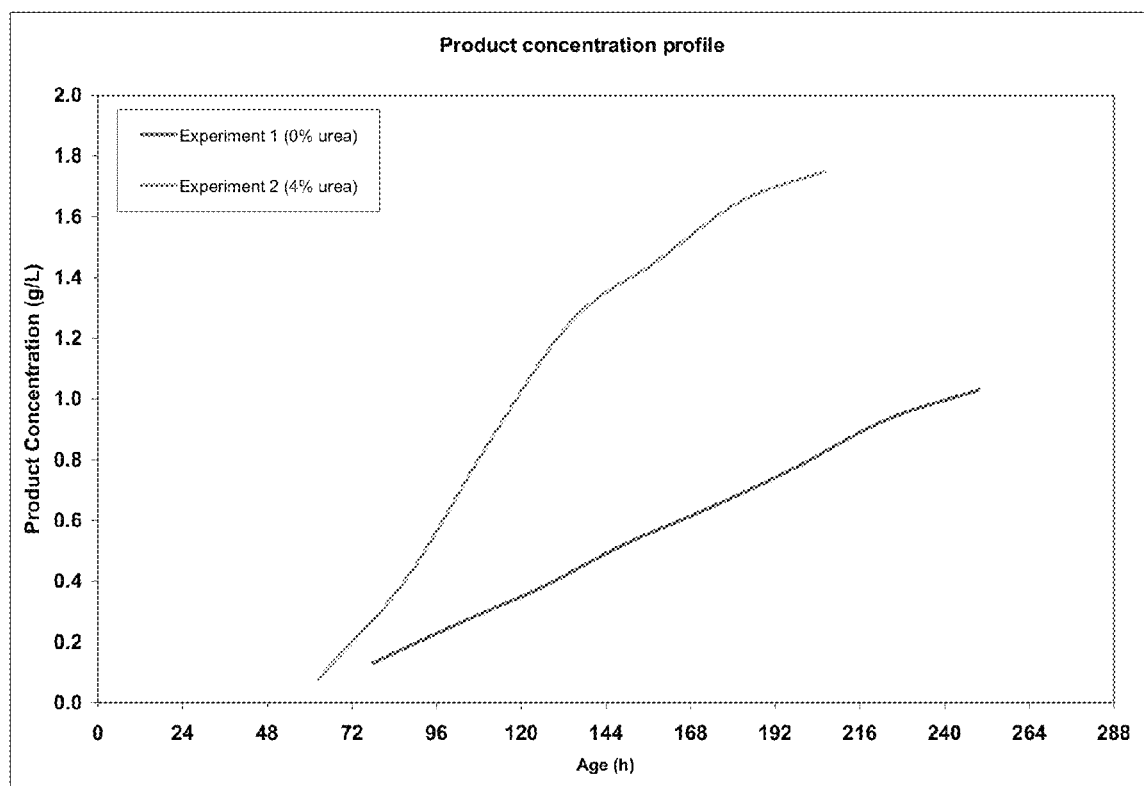
FIG. 6: Comparison of product concentration profile of Glargine precursor with/without urea addition.

Two fermentor batches were run using *Pichia pastoris* for expression of Glargine precursor. In one batch (experiment #1) half of Control media strength is taken as initial medium except glycerol. After batch run methanol is fed at 8 g/L/h feed rate. Fermentation is continued for 10 days. Maximum product concentration reached to 1.03 g/L within 10 days and stabilized. In another batch (experiment #2) same media composition is used and additionally 0.1 M urea is added to intial fermentation medium. After batch run methanol with 4% urea is fed. Fermentation was continued for 9 days. Maximum product concentration reached to 1.75 within 9 days. There was no significant difference observed on cell growth profile. Biomass and product concentration profiles resulting from the above experimentation are represented in FIGS. 5 & 6 respectively.

Example 4

Figure 7:
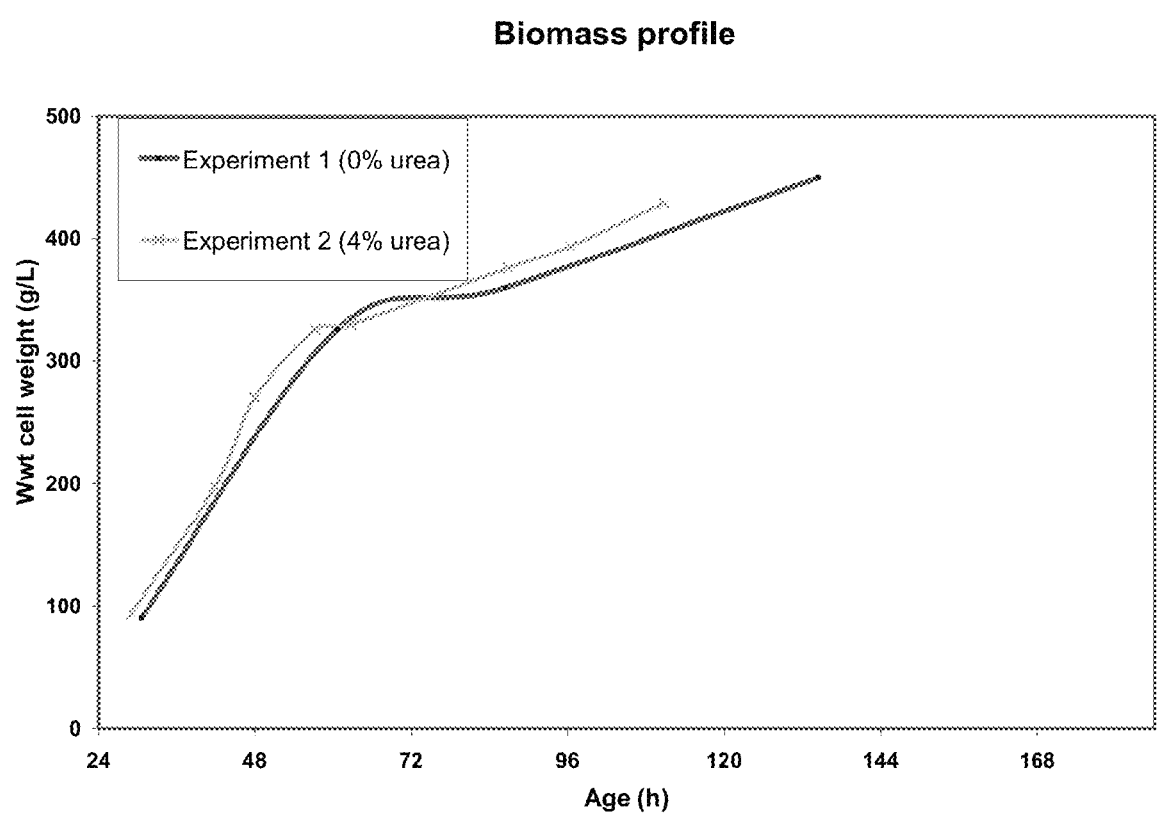
FIG. 7: Comparison of biomass profile of Exendin precursor with/without urea addition.
Figure 8:
FIG. 8: Comparison of product concentration profile of Exendin precursor with/without urea addition.

Two fermentor batches were run using *Pichia pastoris* for expression of Exendin precursor. In one batch (experiment #1) half of Control media strength is taken as initial medium except glycerol with glycerol fed batch. After glycerol fed batch run methanol is fed at 11 g/L/h feed rate. Fermentation is continued for 6 days. Maximum product concentration reached to 0.74 g/L within 6 days and stabilized. In another batch (experiment #2) same media composition is used and additionally 0.1M urea is added to fermentor. After batch run methanol with 4% urea is fed. Fermentation was continued for 5 days. Maximum product concentration reached to 0.78 within 5 days. There was no significant difference observed on cell growth profile. Biomass and product concentration profiles resulting from the above experimentation are represented in FIGS. 7 & 8 respectively.

Example 5

Figure 9:
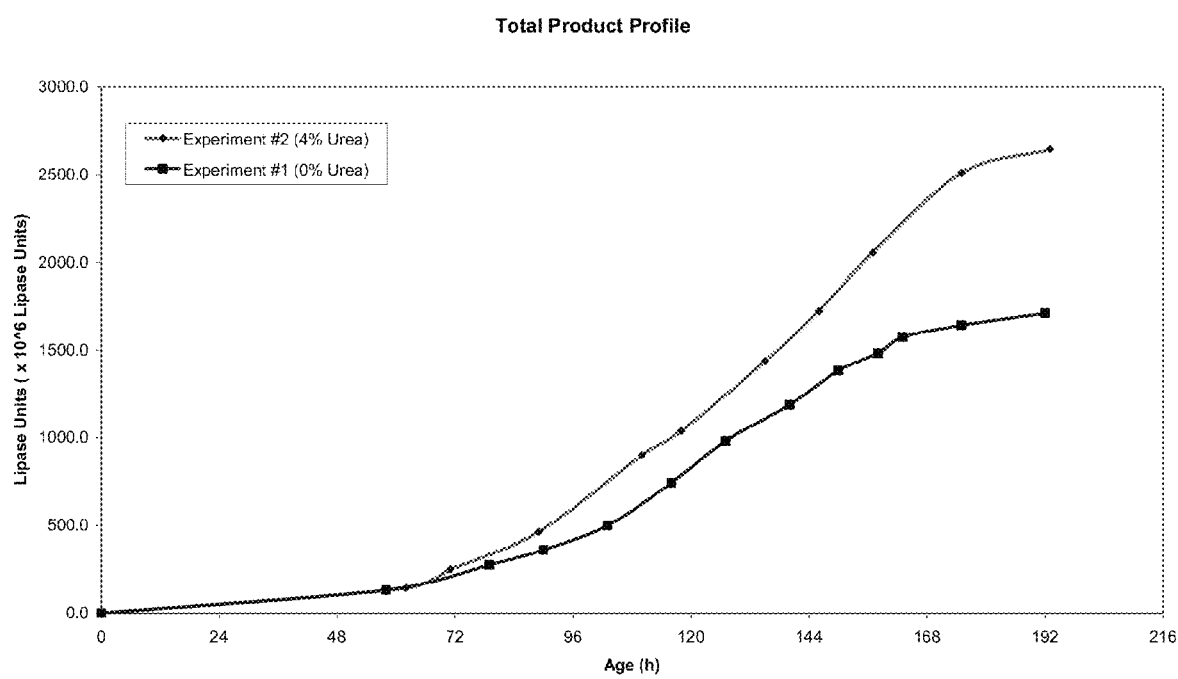
FIG. 9: Comparison of product concentration profile of lipase enzyme with/without urea addition

Two fermentor batches were run using *Pichia pastoris* for expression of the enzyme, Lipase. In one batch (experiment #1) half of Control media strength is taken as initial medium except glycerol. After batch run methanol is fed at about 6 g/L/h feed rate. Fermentation is continued for ~8 days. Maximum product reached to around $1650 \times 10^6$ Lipase Units within 7 days and stabilized. In another batch (experiment #2) same media composition is used and additionally 0.1M urea is added to fermentor. After batch run methanol along with 4% w/v urea is fed. Fermentation was continued for 8 days. Maximum product quantity reached to around $2500 \times 10^6$ Lipase Units within 7 days and then stabilized. There was no significant difference observed on cell growth profile. The total Product profile resulting from the above experimentation is represented in FIG. 9.

Example 6

Figure 10:
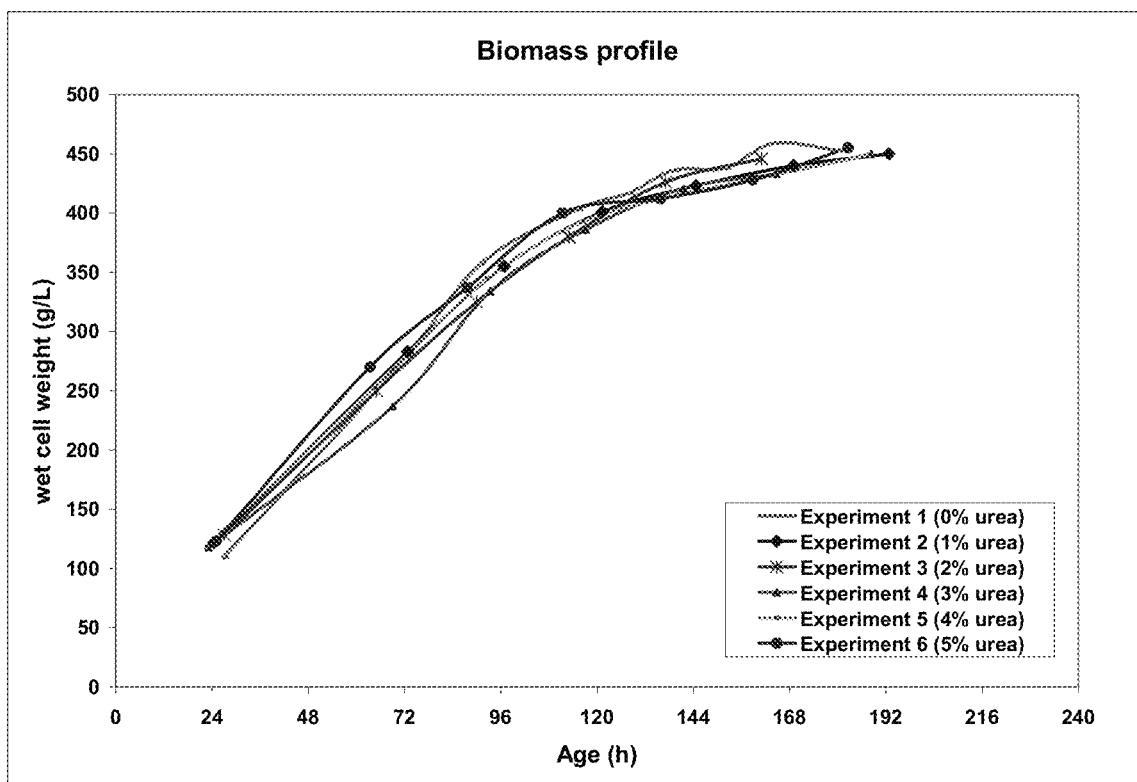
FIG. 10: Biomass profiles resulting from of various concentration of urea during IN-105 precursor fermentation.
Figure 11:
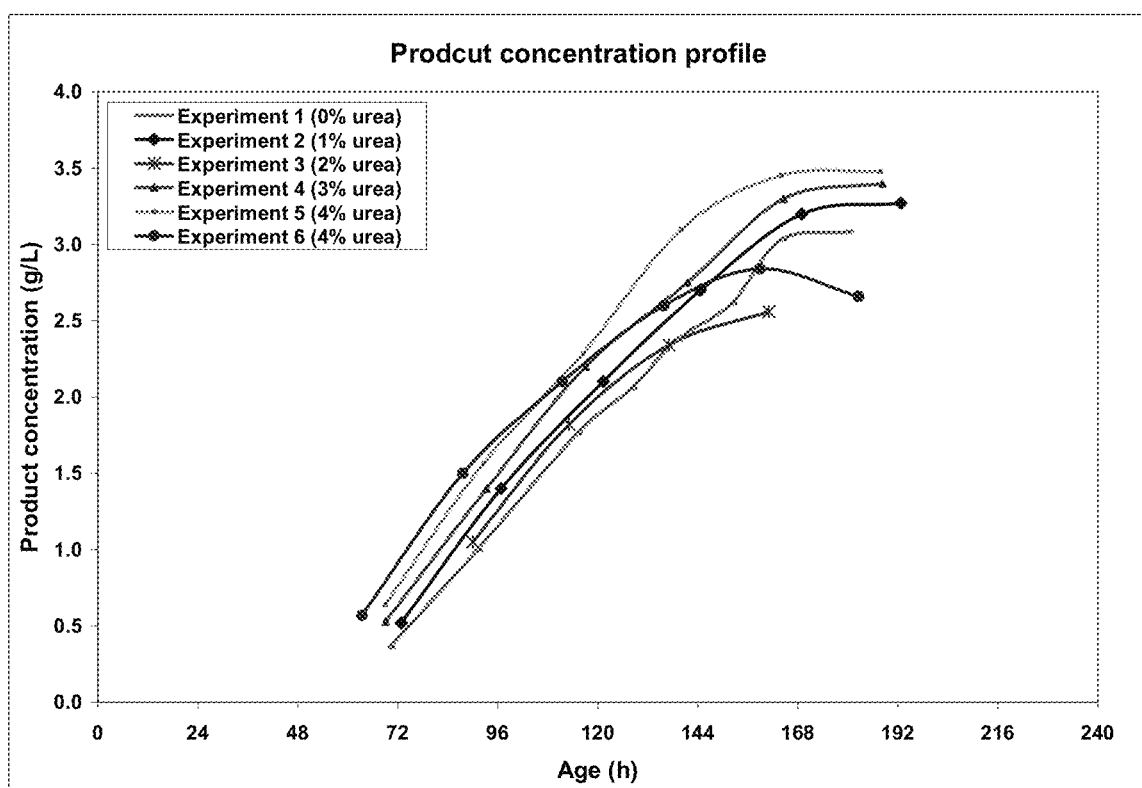
FIG. 11: Product Concentration profiles resulting from of various concentration of urea during IN-105 precursor fermentation.

The effect of urea concentration in methanol batches taken for production of IN105 precursor with 1, 2, 3 and 5% urea in methanol during methanol fed batch was studied. Remaining parameters were kept same as in Example 1. Maximum product concentration reached to 3.0, 3.2, 2.5, 3.3, 3.5 and 2.8 g/L in ~7 days in batches with 0, 1, 2, 3, 4 and 5% urea respectively in methanol. Better productivity was observed when 4% urea was used in methanol during methanol induction phase. Biomass and product concentration profiles are illustrated in FIGS. 10 & 11 respectively.

Example 7

Figure 12:
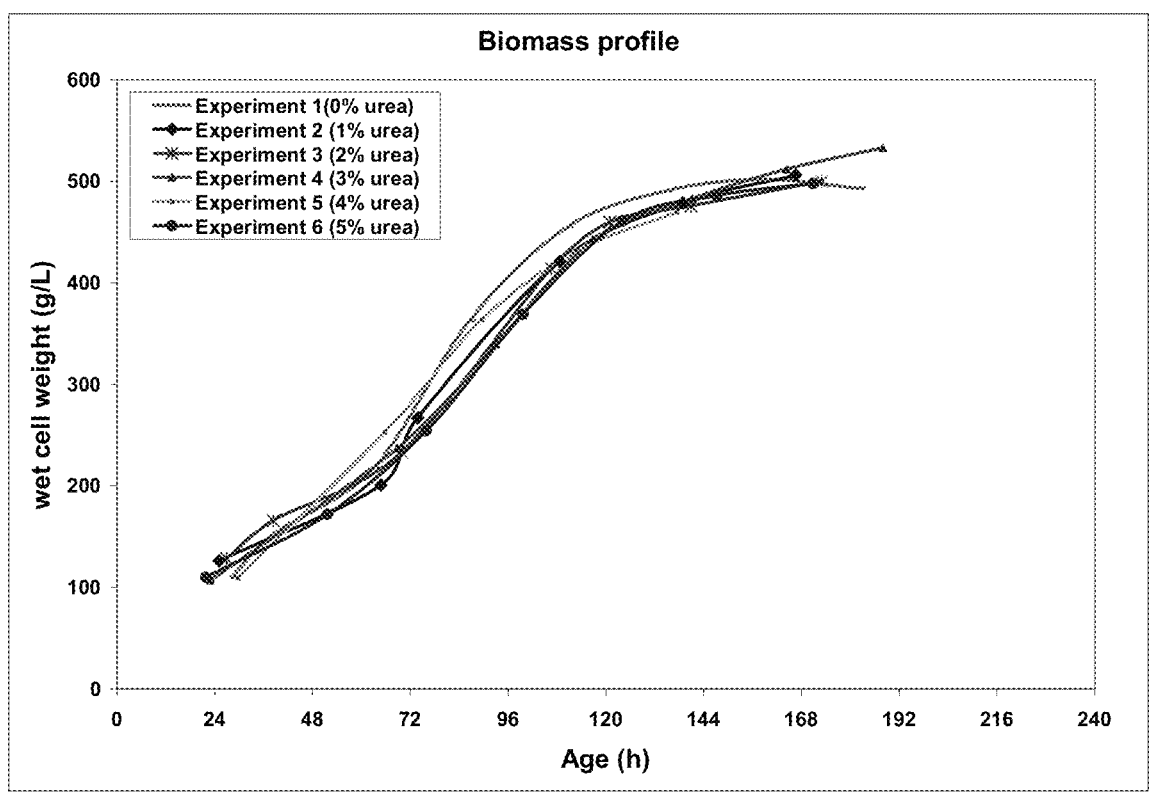
FIG. 12: Biomass profiles resulting from of various concentration of urea during Insulin precursor fermentation.
Figure 13:
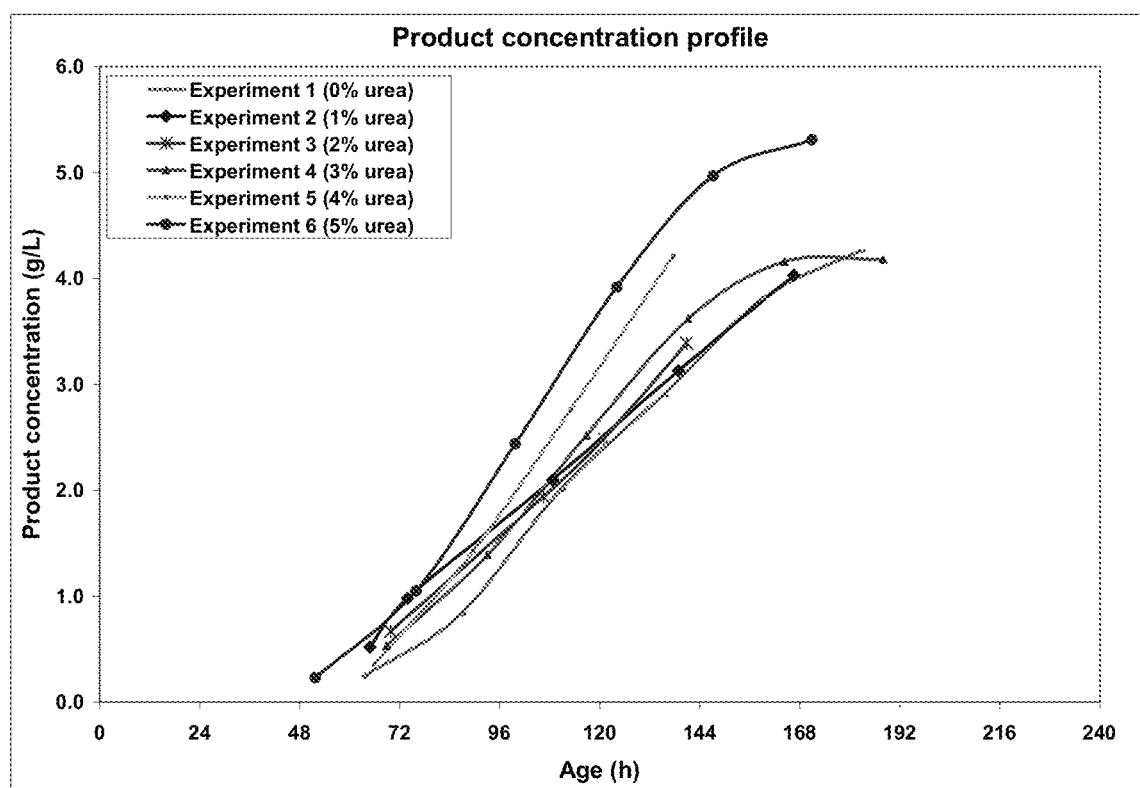
FIG. 13: Product Concentration profiles resulting from of various concentration of urea during insulin precursor fermentation.

In another trial with 20 g/L/h of methanol feed rate, concentration of urea was varied to ascertain the most effective concentration of urea enabling maximum insulin precursor concentration. Maximum product concentration reached to 4.26, 4.03, 3.39, 4.16, 4.21 and 5.31 g/L in 182, 166, 140, 164, 137 and 170 hour respectively in batches where methanol is fed with 0, 1, 2, 3, 4 and 5% urea concentration respectively. Biomass and product concentration profiles are illustrated in FIGS. 12 & 13 respectively. The trial indicated that addition of urea increased the rate of insulin precursor production, the rate of expression being the highest when methanol is fed with 5% of urea.

Example 8

Trial batches were studied where during methanol induction phase, residual urea concentration is maintained at different levels of 0.1, 0.3, 0.5, 0.7, 1.2 and 1.5M in cell free supernatant and the effect on productivity was studied. All the batches were taken with similar parameters and media composition as in Example 1. Residual urea was maintained by feeding urea stock separately. Results indicate that maximum product was achieved when urea is maintained with the range of 1M in cell free supernatant during fermentation throughout the batch. Maximum product concentration 4.46 g/L is achieved when residual urea is maintained about 0.5 M.

Figure 14:
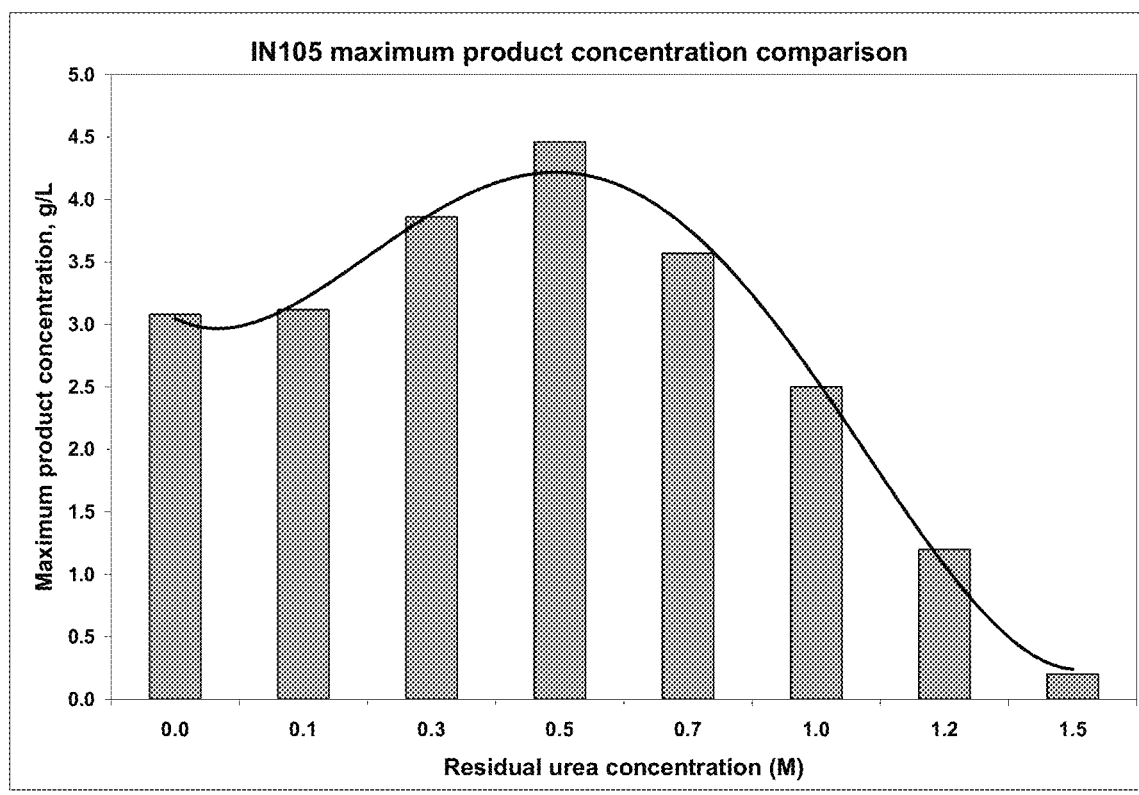
FIG. 14: Residual Urea concentration and maximum product concentration for IN-105 production.

In this experiment the total urea fed was equivalent to 0, 0.2, 0.5, 0.9, 1.2, 1.8, 2.3 and 2.9 M of final broth volume in trials where residual urea was maintained at 0, 0.1, 0.3, 0.5, 0.7, 1.0, 1.2 and 1.5 M respectively. The results are represented in FIG. 14.

Example 9

Figure 15:
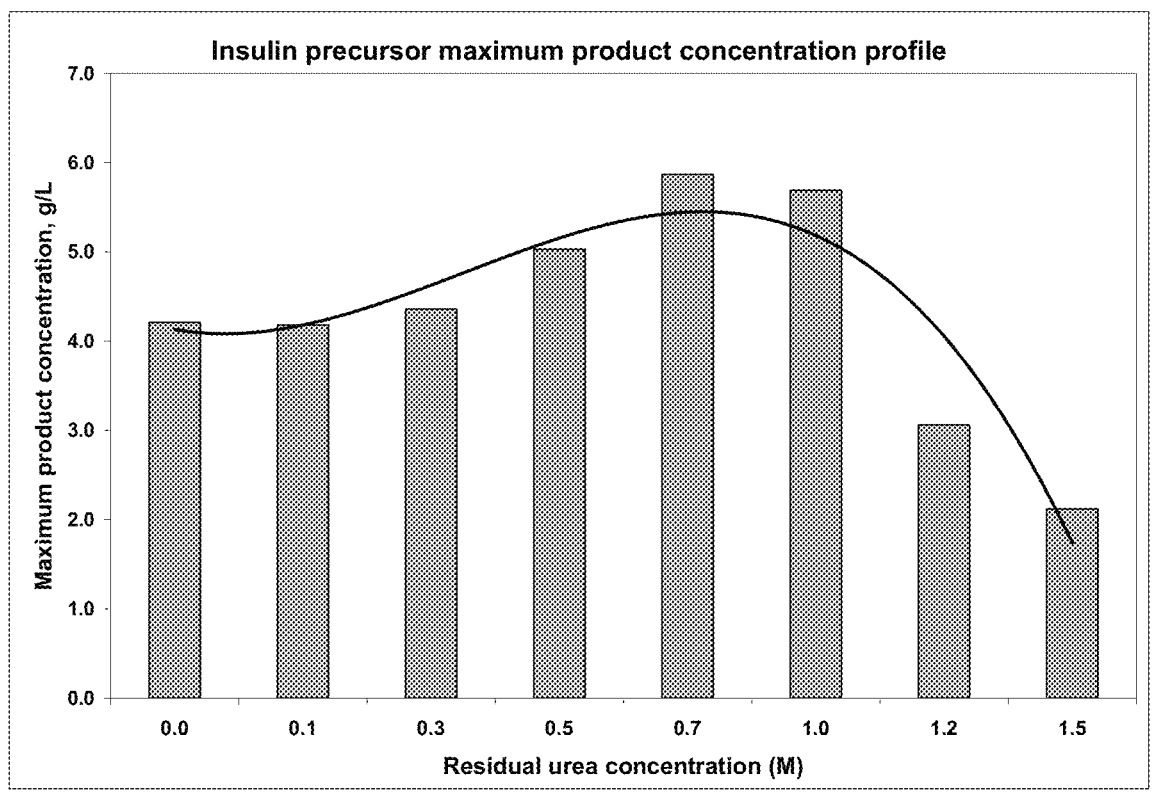
FIG. 15: Residual Urea concentration and maximum product concentration profile for Insulin precursor production.

Trial with Insulin precursor fermentation was also done. In this trial methanol was fed at the rate of 20 g/L/h. In insulin precursor fermentation it was observed that product concentration was highest when 0.7 M residual concentration was maintained. In this trial total urea was fed equivalent to 0.0, 1.6, 2.7, 3.5, 7.0, 8.8, 11.7 and 13.3M of final broth volume in trial where residual urea was maintained to 0, 0.1, 0.3, 0.5, 0.7, 1.0, 1.2 and 1.5M respectively. Results indicated that culture could consume significant quantities of urea as represented in FIG. 15.

Example 10

Figure 16:
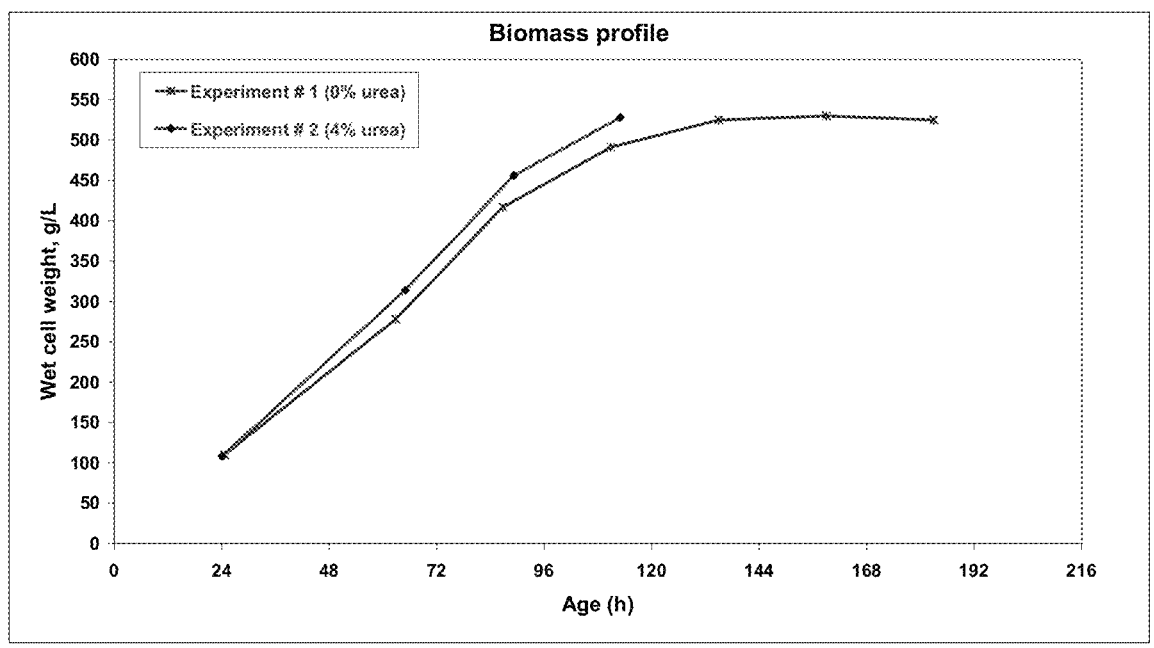
FIG. 16: Comparison of biomass profile of IN-105 precursor with methanol feed rate of ~20 g/L/h
Figure 17:
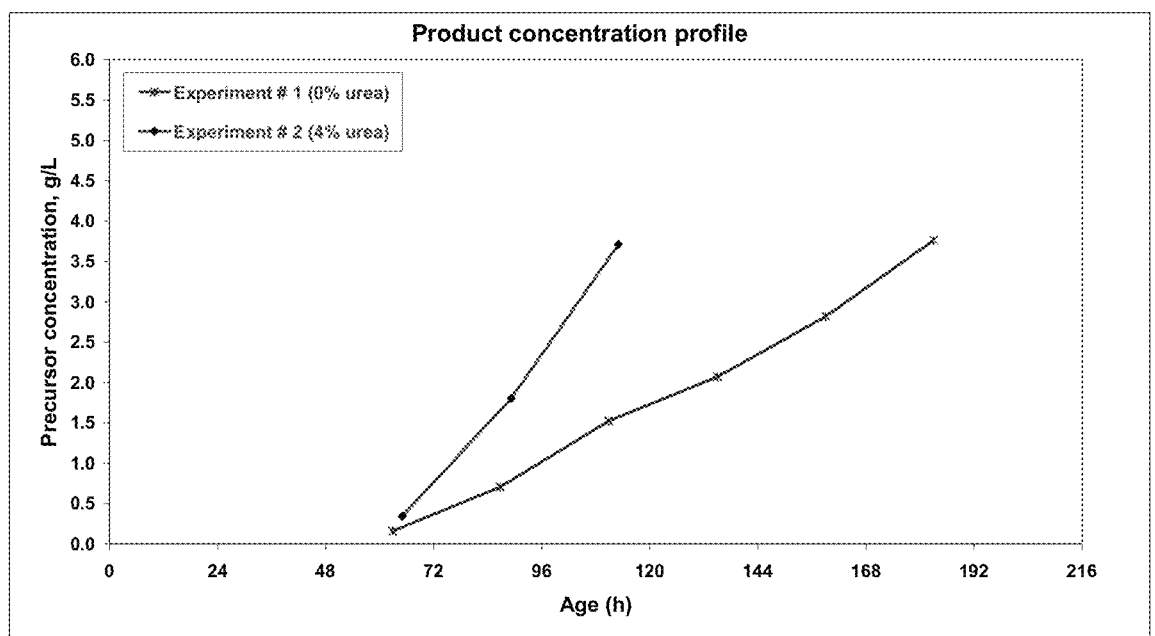
FIG. 17: Comparison of product concentration profile of IN-105 precursor with methanol feed rate of ~20 g/L/h.

Another batch of IN105 was run with standard Control media and with ~20 g/L/h of methanol with 4% urea it. In this trial 3.71 g/L product concentration achieved in 113 hours as against a yield of 3.76 g/L in 183 hours when no urea was fed to the fermentor. The results of the study are illustrated in FIGS. 16 & 17.

Example 11

Figure 18:
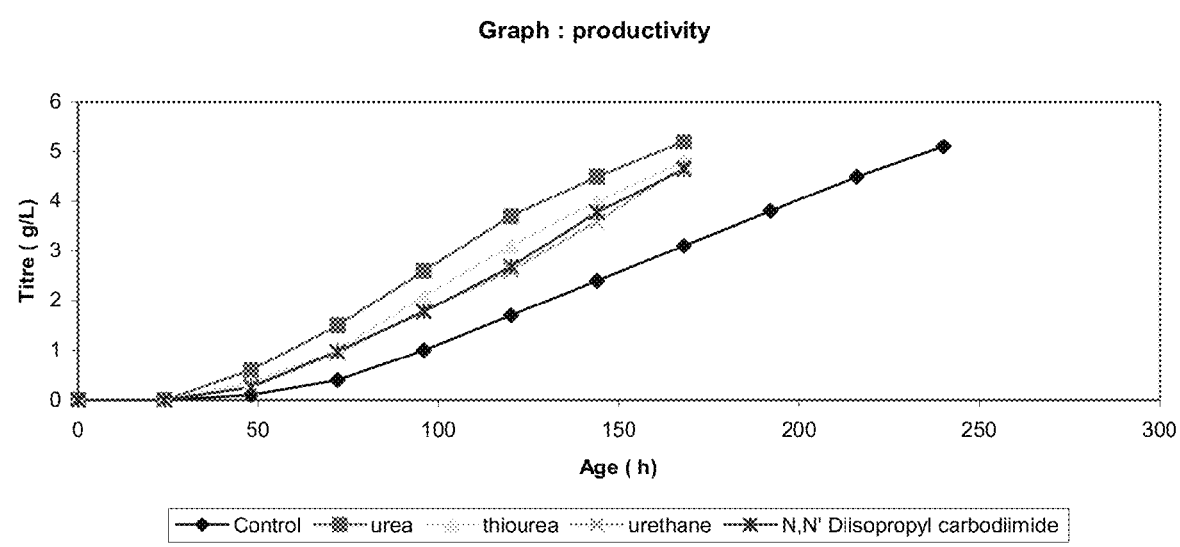
FIG. 18: Study of compounds other than urea, Testing of other similar compounds for their impact upon productivity of *Pichia* fermentation
Figure 19:
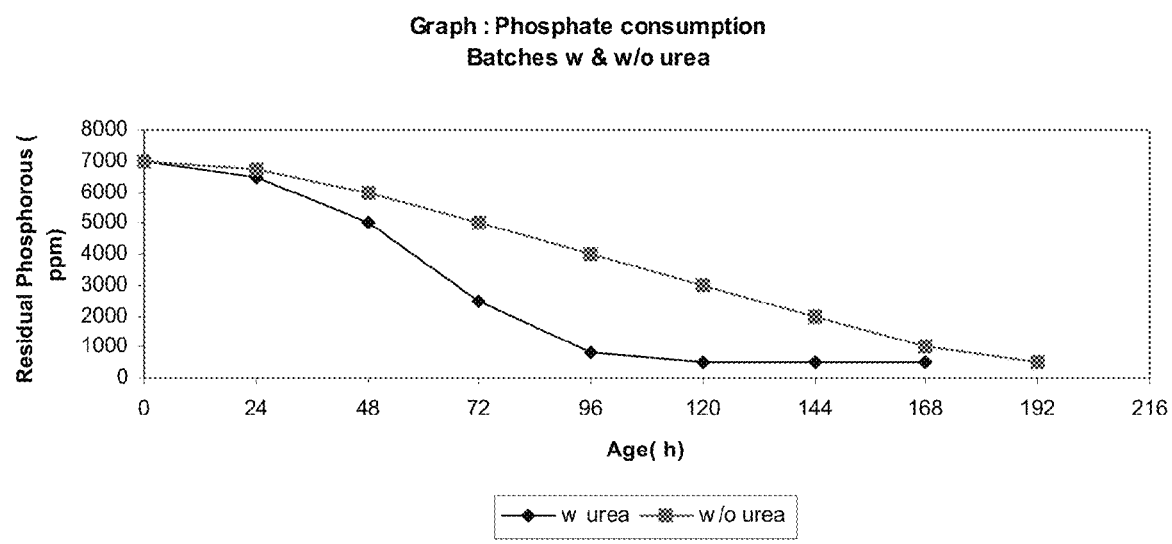
FIG. 19: Effect of urea upon residual concentration of phosphate ions in the broth, Effect of urea upon phosphate metabolism by the strain FIG. 20. Culture growth profile for Pravastatin production FIG. 21. Titre of Pravastatin with urea addition FIG. 22. Percentage conversion of Compactin of Pravastatin with urea addition FIG. 23. WCW comparison of G-CSF production in *E. coli*

In further set of experiments, urea was replaced with various other compounds to observe their effects on fermentation productivity. Thus, in separate batches, thiourea, diimides, carbodiimides, thiocarbamides were tested at 1% concentration. It was observed that all of them improved the productivity with respect to control as shown in FIG. 18.

Example 12

In an experiment, it was observed that feeding of urea during fermentation, increases the uptake of phosphate by the yeast resulting in depletion of phosphate in the medium earlier than a batch where urea feeding has not been done. Thus, faster phosphate consumption and higher productivity (g/L/h) is a result of metabolic shift achieved due to incorporation of urea into standard or modified *Pichia* fermentation protocols for production of peptides and proteins.

Example 13

The growth medium was prepared containing Soya bean flour 5.0 grams, Dextrose monohydrate 20.0 grams, Soy peptone 5.0 grams, CaCO3 1.0 grams, K2HPO4 0.1 grams in 1000 ml of water. The pH of the seed medium was adjusted to 6.8±0.1 with a NaOH solution. The sterilized inoculum medium was inoculated with a spore vial suspension of culture, *Streptomyces* sp (BICC 6826), and incubated at 28±1° C. for 48 hours under aerobic conditions. The grown seed is then transferred to the fermentation medium containing soya bean flour 37.5 grams, Dextrose Monohydrate 22.5 grams, Cotton Seed Flour 3.75 grams, corn steep liquor 7.5, NaCl 7.5 and Antifoam SAG 0.5 gram in 1000 ml of water (ph adjusted to 7.0±0.1). After 48 hrs of incubation, sterile compactin solution was added along with small quantities of dextrose. After every 24 hours, one of the flasks from several similar flasks is harvested to check for the bioconversion of compactin to pravastatin. The procedure was repeated every 24 hours till a total of 3.0 g/L of Compactin had been fed.

Figure 20:
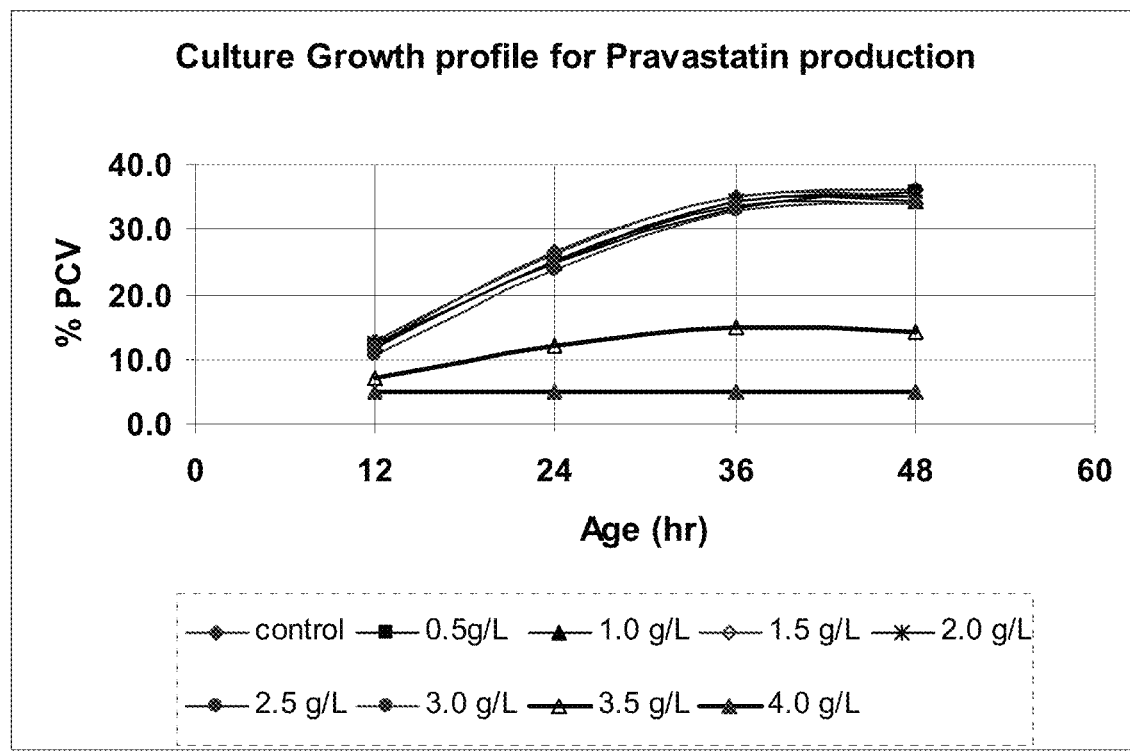

Prior to initiation of experiments using the modified fermentation medium, different levels of urea were added to fermentation medium to establish the toxicity level of urea for the organism. A concentration of 0.0, 0.5, 1.0, 1.5, 2.0, 2.5, 3.0, 3.5 and 4.0 g/L was added to the flask containing the fermentation medium then incubated as discussed above. After 48 hours of incubation, the growth in each of the flask was monitored. The data is shown in FIG. 20.

Concentrations more than 3.0 g/L of urea showed inhibition on the growth of the culture. The trial when repeated showed similar results. So concentration below 3.0 g/L was taken for checking the effect of urea on bioconversion As described previously, a similar exercise was done with the production medium containing urea as an additional constituent. The concentration of urea in the production medium was kept at 0.0, 0.5, 1.0, 1.5, 2.0, 2.5, and 3.0 g/L and it was added at the time of inoculation.

Figure 21:
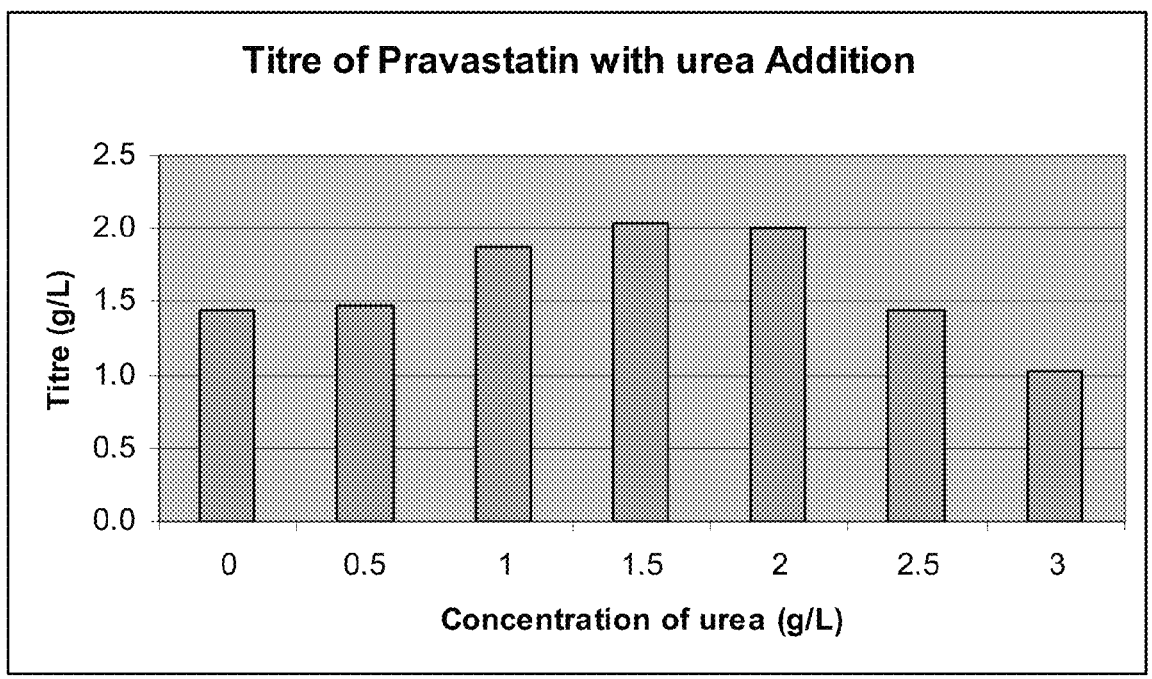
Figure 22:
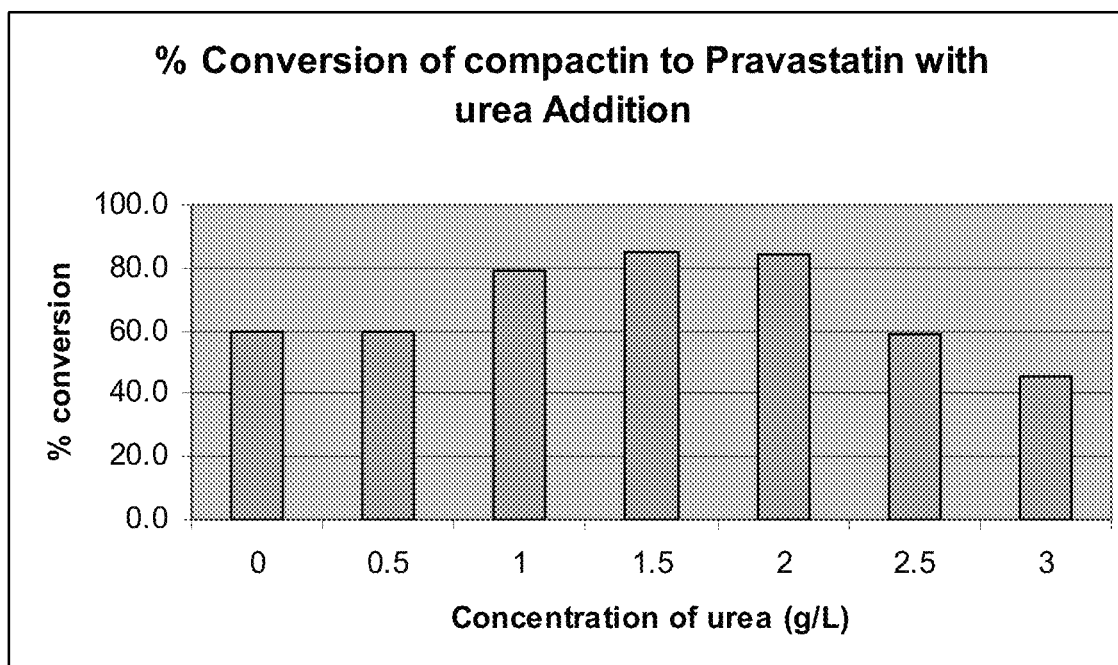

After 48 hrs of incubation, sterile Compactin solution was fed along with dextrose feed. The bioconversion was estimated after 24 hrs by harvesting one of the multiple flasks running under similar conditions. This procedure was repeated every 24 hrs till 3 g/l of compactin was fed cumulatively. Bioconversion was estimated with respect to total Compactin consumed for the formation of Pravastatin. The results of the experiment with respect of titer and percentage conversion are shown in FIGS. 21 and 22 respectively.

The flasks with urea concentration 1.5 g/L showed maximum conversion of compactin to pravastatin of 85.4% as compared to the control flask with 59.5% conversion.

Example 14

Expression of Granulocyte colony stimulating factor (GCSF) with urea was studied using *E. coli* fermentation to ascertain the rate of product expression. The medium used in the trial consisted of a pre-seed medium, seed medium and the production medium. The pre-seed medium consisted of Soya peptone 10.0 g, NaCl 10.0 g, yeast extract 10.0 g in 1000 ml of water. The seed medium consisted of 1.2 g Ammonium sulphate, 2.4 g of Magnesium sulphate, 10 g Yeast extract, 11 g DMH, 5 g K2HPO4, 40 ml Trace salts in 1000 ml of water. The production medium consisted of dextrose monohydrate 11 g, Ammonium sulphate 2.4 g, Magnesium sulphate 4.8 g, yeast extract 20 g, K2HPO4 10 g, Trace salts 40 ml in 1000 ml of water. The ph is adjusted to 7.0 with ammonia. After the batch phase is completed, the biomass in the fermenter is increased by continuous feeding of dextrose and yeast extract. The ceel mass is then induced and run for another 8 hours for the production of the product o concern.

Three fermenter batches were taken to establish the effect of urea in E coli fermentation processes. The first batch(experiment #1) was the control batch without any urea addition. The media used is described above. Batch was induced at ~180 g/L WCW. Fermentation was continued upto 8 hrs after induction. The maximum product achieved was 6.6 g/L with a specific activity of 0.028 g/wcw. In the second batch(experiment #2), 1 g/L urea was added to the fermenter in addition to the media described above. The batch was fed with the feed having similar quantities of urea (1 g/L). Batch was induced at ~180 g/L WCW and fermentation was continued for 8 hrs after induction and the product obtained was 7.4 g/L with a specific activity of 0.033 g/WCW. The third batch (experiment #3) was run similar to experiment #2 but with 2 g/L urea. The final product achieved was 6.58 g/L with the specific activity of 0.032 g/wcw.

Figure 23:
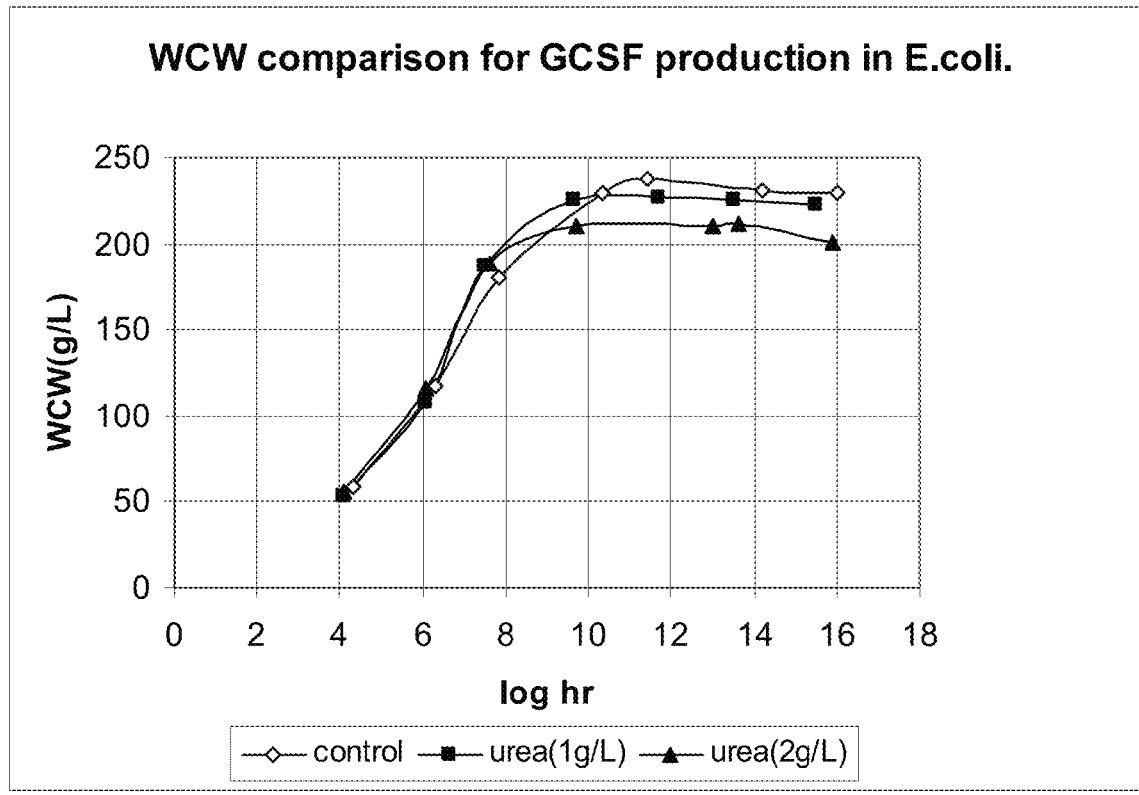
Figure 24:
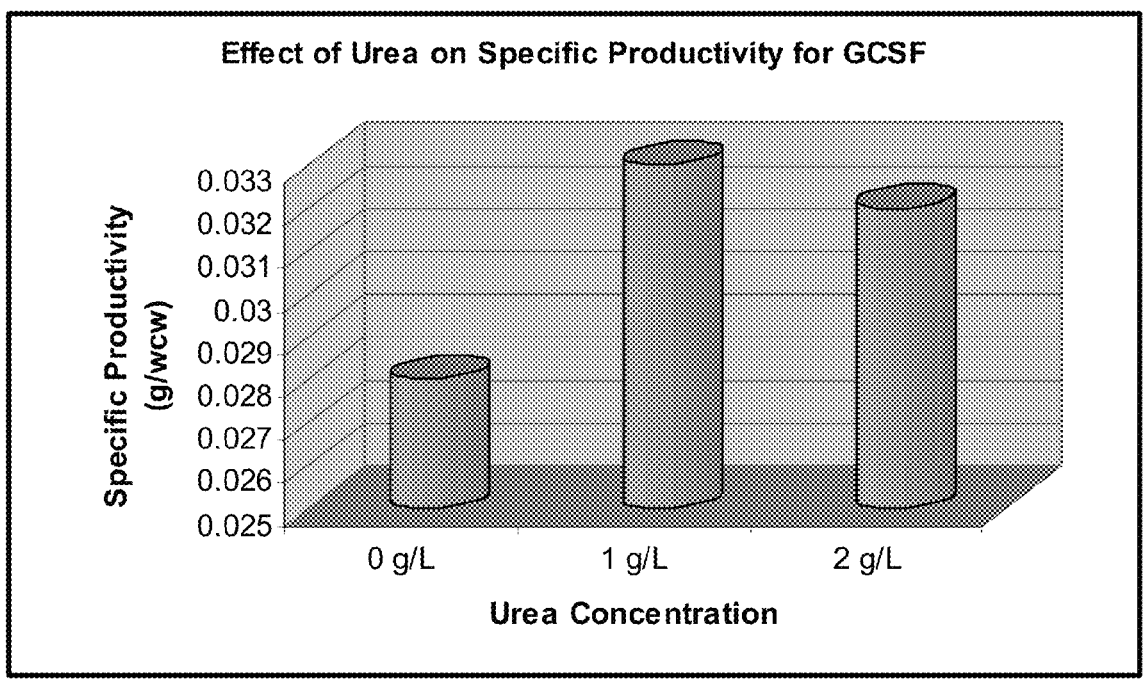
FIG. 24. Effect of urea on specific productivity for GCSF

As the results shows, no significant difference in cell growth profile was observed indicating that urea addition to the fermentor increased the product formation without affecting the growth profile. An overall of about 18% increase in the specific productivity was obtained. WCW profiles resulting from the above experimentation are represented in the FIG. 23 and the specific productivity profile in FIG. 24

Example 15

A similar experiment was done using E. coli as the expression system for the production of Streptokinase. The medium used is same as that mentioned in Example 13 and the urea concentration tested is also the same. As described in Example 14, similar three batches were taken with 0 g/L, 1 g/L and 2 g/L of urea. The control batch without urea (experiment #1) gave the final productivity of 7.06 g/L after 8 hours of induction with the specific productivity of 0.026 g/wcw. The maximum titre was achieved in 1 g/.L urea batch (experiment #2) having productivity of 10.5 g/L and specific productivity of 0.041 g/wcw. Surprisingly the batch with 2 g/L urea (experiment #3) gave only 6.56 g/L of product with specific productivity of 0.022 g/wcw. For this product, an increase in the urea concentration more than 1 g/L resulted in a sharp drop in the specific productivity and titer.

Figure 25:
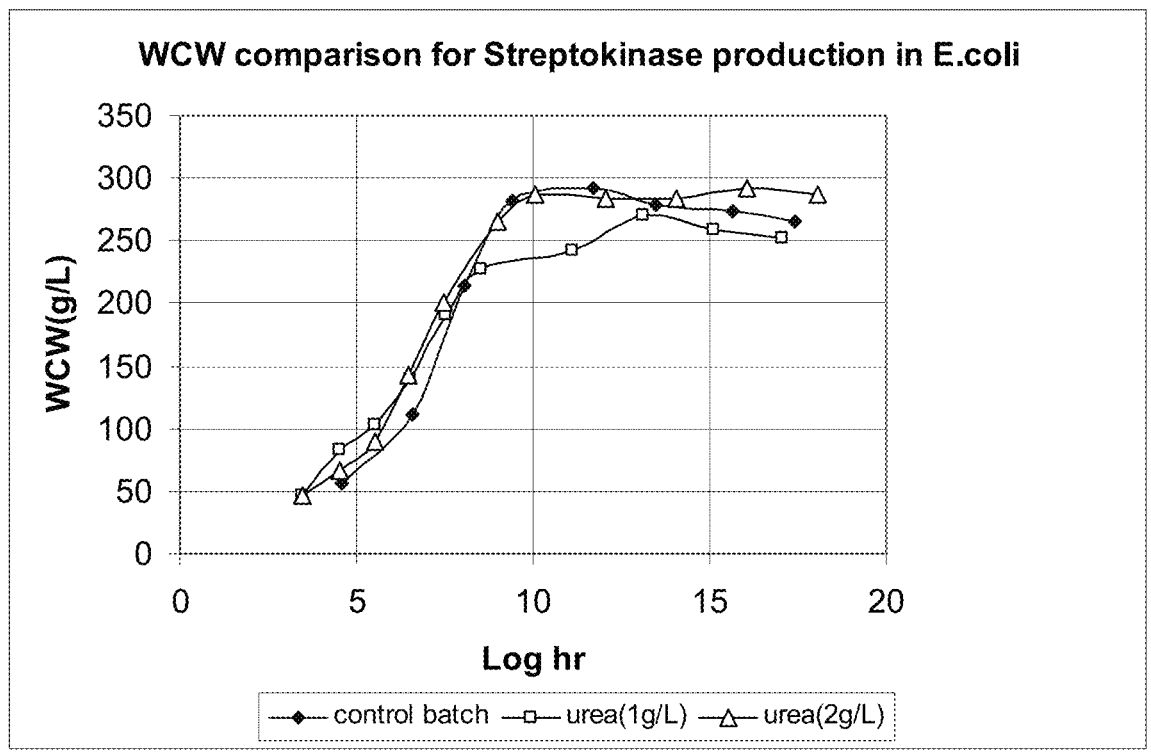
FIG. 25. WCW comparison for streptokinase production in *E. coli*
Figure 26:
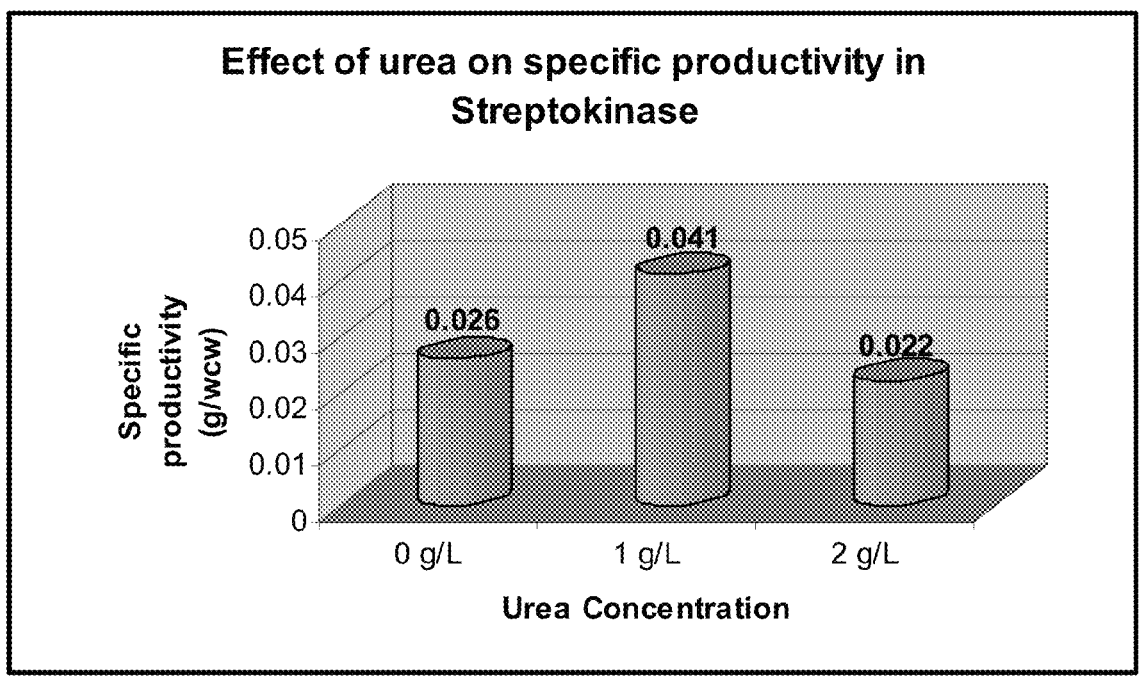
FIG. 26. Effect of urea on specific productivity in Streptokinase

As in Example 2, there was no significant variation s in the WCW of the three trials which clearly indicated that the increase in productivity is the result of increased product formation and not linked to variations in biomass. An overall of about 57% increase in the specific productivity was obtained. WCW profiles resulting from the above experimentation are represented in the FIG. 25. Titre profile is represented in the FIG. 26.

Example 16

Rhizomucor sp (BICC 362) which is known to produce lipase enzyme also showed improvement in productivity with the addition of the urea in the medium. The Lipase generated from this culture can be extensively used for bioconversion reactions like esterification and hydrolysis. Two fermentation batches (10 L volume) were taken with this process, one without urea addition and the other with 0.5 g/L of urea. A trial with higher urea concentration (1 g/l) was also taken which resulted in lower productivities and a very high consumption of caustic to maintain pH. The growth medium for rhizomucor sp (BICC 362) consists of Maida 41.4 g, sucrose 10 g, peptone 3.06 g, ammonium sulphate 2 g, yeast extract 2 g, potassium phosphate, 0.85 g, calcium chloride, magnesium sulphate and sodium chloride 1 g each. The whole medium is made up to 1 L with water. The grown seed (10% v/v) is transferred to the production medium consisting of dextrose 12.5 g, soya peptone 37.5 g, soya flour 25, potassium phosphate 2.5, magnesium sulphate 0.625, soya oil 12.5 g in 1000 ml of water. The pH of the medium is adjusted to 6.0 and then maintained at 6.0 throughout the batch with caustic addition.

Figure 27:
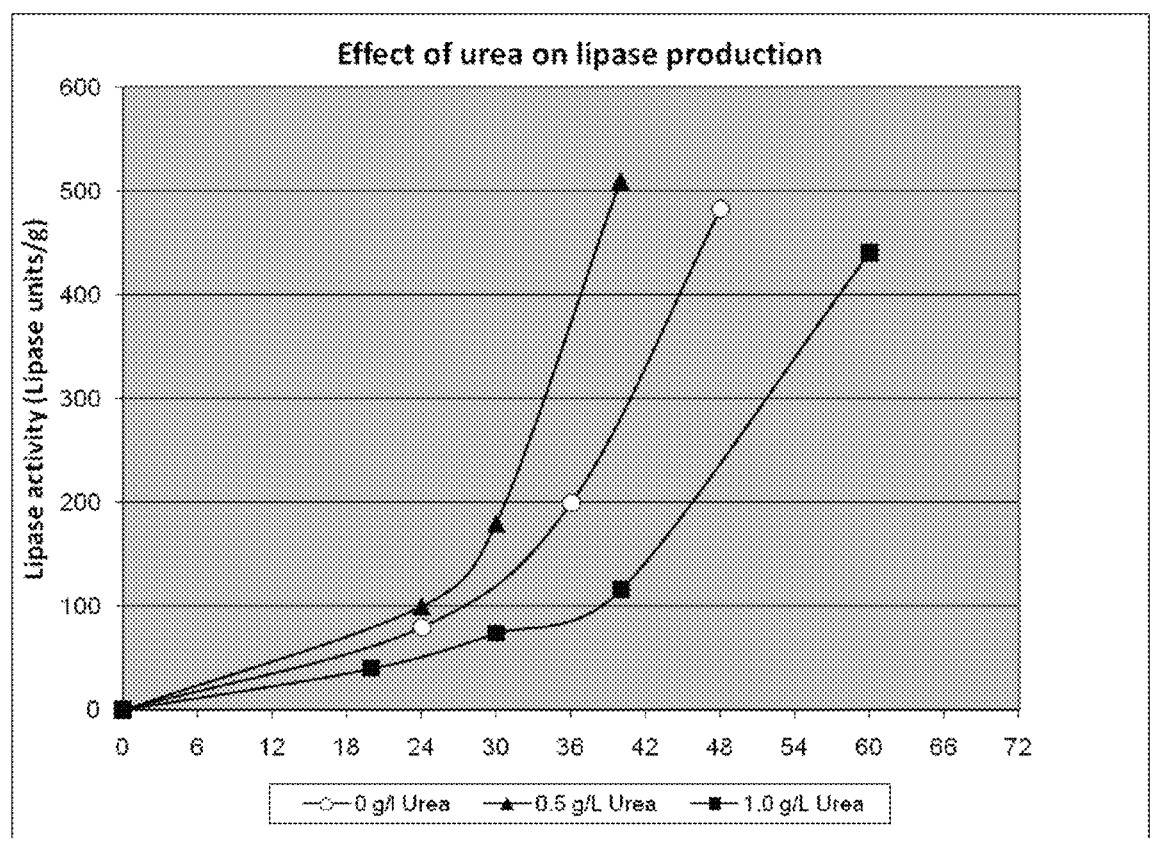
FIG. 27. Effect of urea on the lipase production using a *Rhizomucor* sp

The addition of urea (0.5 g/l) showed an increase in the rate of lipase production as compared to the control batch. Higher concentration of urea showed lower productivities. The data is shown in FIG. 27.

It is to be understood that this invention is not limited to the particular methodology, protocols, cell lines, species or genera, and media components described, as such may vary. It is also to be understood that the terminology used herein is for the purpose of describing particular embodiments only, and is not intended to limit the scope of the present invention which will be limited only by the appended claims. The above description is for the purpose of teaching the person of ordinary skill in the art how to practice the present invention, and it is not intended to detail all those obvious modifications and variations of it which will become apparent to the skilled worker upon reading the description.

We claim:

1. A fermentation medium for production of a recombinant protein or a derivative or analog thereof or a secondary metabolite by improving phosphate uptake through fermentation using a microorganism, said medium characterized in that a residual concentration of urea, a derivative of urea, dimethylurea, diethylurea, N-acetylphenyl urea, isopropylpylideneurea, phenylurea or a combination thereof is maintained in a range of about 0.5 g/L to about 3 g/L, a methanol feeding rate range from about 6 g/L/h to about 20 g/L/h, basal salts per liter comprising:

Phosphoric acid (85%): from about 2.67 ml to about 133.5 mL,
Calcium sulfate: from about 0.093 g to about 4.65 g,
Potassium sulfate: from about 1.82 g to about 91 g,
Magnesium sulfate-7$H_2O$: from about 1.49 g to about 74.5 g,
Potassium hydroxide: from about 0.413 g to about 20.65 g,
Glycerol: from about 4 g to about 200 g;

and trace elements per liter comprising:
Cupric sulfate.5$H_2O$: from about 0.6 g to about 30 g,
Sodium iodide: from about 0.008 g to about 0.4 g,
Manganese sulfate-$H_2O$: from about 0.3 g to about 15 g,
Sodium molybdate-2$H_2O$: from about 0.02 g to about 1 g,
Boric Acid: from about 0.002 g to about 0.1 g,
Cobalt chloride: from about 0.05 g to about 2.5 g,
Zinc chloride: from about 2 g to about 100 g,
Ferrous sulfate-7 $H_2O$: from about 6.5 g to about 325 g,
Biotin: from about 0.02 g to about 1 g, and
Sulfuric Acid: from about 0.5 ml to about 25 ml.

2. The fermentation medium according to claim 1, wherein the urea added in liquid, spray, powder or pellet form, and wherein the microorganism is selected from the group comprising *E. coli, Streptomyces* sp, *Aspergillus* sp, *Rhizopus* sp, *Penillium* sp, *and Rhizomucor* sp.

3. The fermentation medium according to claim 1, further comprising the recombinant protein, wherein the recombinant protein is selected from the group comprising G-CSF, streptokinase and lipase; and wherein the secondary metabolite is pravastatin.

4. The fermentation medium according to claim 1, further comprising the recombinant protein, wherein the recombinant protein or a derivative or analog thereof yields a maximum product titre of above 0.5 g/L; and wherein the secondary metabolite effectuates bioconversion of compactin to pravastatin by at least 35%.

5. A process for production of a recombinant or non-recombinant protein product or a derivative or analog thereof or a secondary metabolite in the fermentation medium of claim 1, said process comprising steps of
   a) propagating a microorganism in said medium, and
   b) maintaining the residual concentration of urea, a derivative of urea, dimethylurea, diethylurea, N-acetylphenyl urea, isopropylpylideneurea, phenylurea or a combination thereof in a range from about 0.5 g/L to about 3 g/L for production of said recombinant or non-recombinant protein product or a derivative or analog thereof or a secondary metabolite.

6. The process according to claim 5, wherein the urea added in liquid, spray, powder or pellet form; wherein the microorganism is selected from the group comprising *E. coli, Streptomyces* sp, *Aspergillus* sp, *Rhizopus* sp, *Penillium* sp, and *Rhizomucor* sp.

7. The process according to claim 5, wherein the recombinant protein product produced is G-CSF, streptokinase and lipase.

8. The process according to claim 5, wherein the secondary metabolite produced is pravastatin.

9. The process as claimed in claim 5, wherein the recombinant protein, or a derivative or analog thereof, yield a maximum product titre of above 0.5 g/L.

10. The process as claimed in claim 5, wherein the secondary metabolite effectuates bioconversion of compactin to pravastatin by at least 35%.

* * * * *